(12) United States Patent
de Jonge et al.

(10) Patent No.: US 12,336,806 B2
(45) Date of Patent: Jun. 24, 2025

(54) BREATH SAMPLER

(71) Applicant: Stichting Radboud universitair medisch centrum, Nijmegen (NL)

(72) Inventors: Marinus Isaäk de Jonge, Nijmegen (NL); Cornelis Hubertus van den Kieboom, Utrecht (NL); Michèl Mathijs Klerks, Vlijmen (NL); Ronald van Doorn, Driel (NL)

(73) Assignee: Stichting Radboud universitair medisch centrum, Nijmegen (NL)

( * ) Notice: Subject to any disclaimer, the term of this patent is extended or adjusted under 35 U.S.C. 154(b) by 1028 days.

(21) Appl. No.: 17/275,701

(22) PCT Filed: Sep. 13, 2019

(86) PCT No.: PCT/EP2019/074580
§ 371 (c)(1),
(2) Date: Mar. 12, 2021

(87) PCT Pub. No.: WO2020/053431
PCT Pub. Date: Jan. 9, 2020

(65) Prior Publication Data
US 2022/0031189 A1 Feb. 3, 2022

(30) Foreign Application Priority Data

Sep. 14, 2018 (NL) ...................... 2021637

(51) Int. Cl.
*A61B 5/08* (2006.01)
*A61B 5/091* (2006.01)
(Continued)

(52) U.S. Cl.
CPC .............. *A61B 5/082* (2013.01); *A61B 5/091* (2013.01); *A61B 5/097* (2013.01); *A61B 2010/0087* (2013.01)

(58) Field of Classification Search
CPC ......... A61B 5/082; A61B 5/087; A61B 5/091; A61B 5/097; A61B 2010/0083; A61B 2010/0087; A61B 2560/0431
See application file for complete search history.

(56) References Cited

U.S. PATENT DOCUMENTS

| 3,661,528 A | 5/1972 | Falk |
| 4,538,620 A | 9/1985 | Nowacki et al. |

(Continued)

FOREIGN PATENT DOCUMENTS

| CN | 201061535 Y | 5/2008 |
| CN | 104799820 A | 7/2015 |

(Continued)

*Primary Examiner* — Jay B Shah
*Assistant Examiner* — Andrew E Hoffpauir
(74) *Attorney, Agent, or Firm* — N.V. Nederlandsch Octrooibureau

(57) ABSTRACT

A breath sampler for collecting a breath sample from a patient is disclosed. The breath sampler has a non-rebreather part including a sample inlet, a one-way outlet valve downstream of the sample inlet, and an air inlet. The one-way outlet valve and the sample inlet define a first portion of an internal breath flow pathway therebetween. The air inlet is arranged to be closed by a one-way inlet valve arranged to allow air to enter the non-rebreather part. The breath sampler also has a sample delivery part in fluid communication with the non-rebreather part at an upstream end via the one-way outlet valve. The sample delivery part defines a second portion of the internal breath flow pathway, and has an air diverter, a sample outlet, a return inlet and a sample collection chamber connector. The air diverter is arranged to divide the sample delivery part into an upstream portion upstream of the air diverter and a downstream portion downstream of the air diverter and is configured to divert the breath sample into a sample collection chamber including a liquid capture interface. The sample collection chamber is (Continued)

coupled to the sample collection chamber connector and includes a liquid capture interface.

20 Claims, 15 Drawing Sheets

(51) Int. Cl.
*A61B 5/097* (2006.01)
*A61B 10/00* (2006.01)

(56) References Cited

U.S. PATENT DOCUMENTS

| | | | | |
|---|---|---|---|---|
| 5,465,728 | A * | 11/1995 | Phillips | A61B 5/097 |
| | | | | 128/204.17 |
| 10,086,166 | B1 * | 10/2018 | Nashed | A61M 16/0891 |
| 10,195,147 | B1 * | 2/2019 | Yadidi | A61M 15/0035 |
| 2004/0077093 | A1 | 4/2004 | Pan | |
| 2004/0138577 | A1 * | 7/2004 | Kline | A61B 5/097 |
| | | | | 600/543 |
| 2005/0137491 | A1 | 6/2005 | Paz et al. | |
| 2007/0173731 | A1 * | 7/2007 | Meka | G01N 33/497 |
| | | | | 600/543 |
| 2010/0121212 | A1 | 5/2010 | Carlsson et al. | |
| 2010/0279271 | A1 | 11/2010 | McCash et al. | |
| 2010/0292601 | A1 * | 11/2010 | Dompeling | A61B 5/411 |
| | | | | 600/543 |
| 2012/0004571 | A1 * | 1/2012 | Ku | A61B 5/082 |
| | | | | 600/562 |
| 2014/0180156 | A1 | 6/2014 | Ku et al. | |
| 2014/0276169 | A1 * | 9/2014 | Chua | A61M 16/0672 |
| | | | | 128/205.24 |
| 2015/0072889 | A1 * | 3/2015 | Lui | C12Q 1/705 |
| | | | | 435/6.12 |
| 2016/0022946 | A1 | 1/2016 | Sislian et al. | |
| 2016/0338616 | A1 * | 11/2016 | Eichler | A61B 5/097 |
| 2017/0035326 | A1 | 2/2017 | King-Smith | |
| 2017/0119280 | A1 * | 5/2017 | Ahmad | A61B 5/097 |
| 2018/0110444 | A1 * | 4/2018 | Sherwood | A61B 5/08 |
| 2021/0093226 | A1 * | 4/2021 | Dr Moschos | B01L 3/5021 |

FOREIGN PATENT DOCUMENTS

| | | | |
|---|---|---|---|
| CN | 107036852 A | 8/2017 | |
| WO | 9531721 A1 | 11/1995 | |
| WO | 2017/153755 A1 | 9/2017 | |
| WO | WO-2018071441 A1 * | 4/2018 | A61M 15/0021 |

* cited by examiner

BREATH SAMPLER

FIELD OF THE INVENTION

The present invention relates to a breath sampler. More particularly, the present invention relates to a breath sampler apparatus for acquiring a breath sample from a user.

BACKGROUND OF THE INVENTION

Diseases of the respiratory tract are a major cause of death worldwide. Conditions that can lead to impaired or reduced respiratory function include acute conditions (such as acute pneumonia, tuberculosis, or other bacterial or viral infections, or lung injuries), and chronic inherited or acquired conditions (such as cystic fibrosis, asthma, chronic obstructive pulmonary disease (COPD), pneumoconiosis and lung cancer).

In particular, there is a growing number of patients suffering from diseases such as chronic obstructive pulmonary disease (COPD), which is a progressive disease resulting in irreversible decreasing function of the pulmonary system. According to the World Health Organization (WHO), COPD is the fourth leading cause of death worldwide, and current data indicates that it will become third leading cause of death by 2030.

There are a wide range of conditions that contribute to COPD, particularly resulting from damage from cigarette smoke or exposure to other irritants. COPD causes breathing difficulties, coughing, wheezing and similar symptoms, and has been correlated to an increased risk of serious conditions such as heart disease and lung cancer.

Patients suffering from COPD (and other chronic respiratory impairments) often experience acute worsening of respiratory symptoms, such as coughing, wheezing, inflammation of the respiratory tract, etc. Approximately 75% of these acute lung attacks in COPD patients are caused by infection. Such lung attacks are associated with further health problems including accelerated loss of lung function, reduction in health-related quality of life and substantial health care costs.

A majority of lung attacks are attributed to bacterial infections, which are typically diagnosed by culturing on an agar plate using sputum from a patient, and typically takes two to three days. Moreover, many patients with compromised respiratory function or those who are extremely unwell are unable to provide a sputum sample.

C-reactive protein (CRP) responses tested in blood samples can be used to distinguish viral infections from bacterial infections, however the results are not always conclusive and, in many cases, would not justify a medical decision on whether or not to treat a patient with antibiotics.

Consequently, many physicians empirically treat COPD patients with broad-spectrum antibiotics before the results of the culture are determined. This leads to an overuse of antibiotics, which are ineffective if a patient is suffering from a non-bacterial infection (such as a viral infection). The unnecessary use of antibiotics results in additional costs and may lead to side effects that negatively affect the health of a patient, and more widely to antibiotic resistance.

There is therefore a need for a rapid and specific means for detecting of lung infections in COPD patients to support a medical decision on treatment with antibiotics.

Breath samplers for collecting breath samples from a patient are known:

WO 95/31721 describes a breath sample collection apparatus for condensing aerosol material from a breath sample on the walls of a cooled sample collection tube. The condensate from the tube is collected in a sample vial before being taken for testing.

US 2014/0180156 A1 describes a breath sampling apparatus comprising a filter for capturing aerosol droplets from exhaled air. A sample from the filter is then analysed for diagnostic biomarkers.

US 2004/077093 A1 describes a method and apparatus to detect the presence of bacteria in a subject. More particularly, the method comprises administering urea to a subject, obtaining a fluid sample from the subject after the administration of the urea and then determining the presence or amount of ammonia gas in the fluid sample.

However, such systems are limited by the additional apparatus required to collect and analyse a viable sample from patients with severely compromised lung function.

SUMMARY OF THE INVENTION

The present invention seeks to overcome some of the problems with known breath samplers by providing a sampler adapted for effective capture of pathogens and other biomarkers from a stream of breath, and through which a patient can breathe normally during a sampling procedure. Aspects of the present invention are therefore directed to a breath sampler configured to deliver a breath sample to a liquid capture interface, whilst allowing the patient to breathe normally. Such a system can be particularly suitable for patients with reduced or limited lung function. It can also allow for longer sampling times, with a greater volume of breath passing through a liquid capture interface, and may thereby lead to improved capture yield and more sensitive testing. The liquid capture interface provides a sample that can be analysed immediately, and is convenient to store and transport.

In a first aspect, the present invention provides a breath sampler for collecting a breath sample from a patient, the sampler comprising a non-rebreather part configured to allow a user to breathe normally during sample collection and a sample delivery part configured to deliver the collected sample to a liquid capture interface. The non-rebreather part comprises a sample inlet and a one-way outlet valve arranged to allow air to exit the non-rebreather part. The one-way outlet valve and the sample inlet defines a first portion of an internal breath flow pathway therebetween. The non-rebreather part further comprises an air inlet in fluid communication with the first portion of the internal breath flow pathway, the air inlet being closed by a one-way inlet valve arranged to allow air to enter the non-rebreather part.

The sample delivery part is in fluid communication with the non-rebreather part at an upstream end via the one-way valve, and defines a second portion of the internal breath flow pathway. An air diverter is provided to divide the sample delivery part into an upstream portion upstream of the air diverter and a downstream portion downstream of the air diverter. The sample delivery part further comprises a sample outlet upstream of the air diverter configured for connection to a sample delivery tube; a return inlet downstream of the air diverter and in fluid communication with the exhaust; and a sample collection chamber connector configured to form a seal with an opening of a sample collection chamber, the connector defining a perimeter; and wherein the sample outlet and the return inlet are disposed within the perimeter.

The breath sample further comprises a sample collection chamber coupled to the sample collection chamber connector, the sample collection chamber comprising a liquid capture interface consisting of a volume of liquid configured to act as a liquid capture medium.

The breath sampler according to the first aspect of the invention can deliver a sample of breath from a patient to the sample collection chamber, whilst allowing the patient to breathe normally. The liquid capture interface can be subsequently tested for target chemical or biological material.

The air diverter is configured to divert the flow of air along the second portion of the internal breath flow pathway, out of the one-way outlet valve and into a sample collection chamber. In some embodiments, air diverter can comprise a wall extending in a plane that is transverse to the longitudinal axis. In at least some embodiments, a wall extends in a plane perpendicular to the longitudinal axis of the sample delivery part. Preferably the air diverter is impermeable to gas and liquid and fluidically separates the upstream portion of the internal breath flow pathway from the downstream portion of the conduit. This forces the air to exit the breath sampler through the sample outlet, to the liquid capture interface.

To deliver the breath sample to the liquid capture interface, the breath sampler can further comprise a sample delivery tube coupled to the sample outlet. The sample delivery tube is coupled to the sample outlet at a proximal end and extends within the sample collection chamber. The sample delivery tube comprises an open distal end configured to be positioned below a surface of the liquid in the sample collection chamber. In at least some embodiments, the open end of the sample delivery tube is disposed toward a distal end of the sample collection chamber. For example, the open end of the sample delivery tube can be disposed within the distal half of the sample collection chamber. More preferably, the open end of the sample delivery tube is disposed within a distal third of the sample collection chamber, more preferably a distal fifth and more preferably a distal tenth of the sample collection chamber.

In at least some embodiments, the breath sampler further comprises a diffuser coupled to the sample delivery tube, the diffuser comprising an inlet (for connection to the open distal end of the sample delivery tube) and a network of channels to divide the sample from the inlet into a plurality of streams. By dividing the breath flow into a plurality of streams, the surface area of sample in contact with the liquid capture medium is increased, thereby increasing the capture yield.

The exhaust outlet is preferably in fluid communication with the atmosphere (i.e. open). It can comprise a filter or mesh (e.g. a bacterial filter) or an open aperture. In some embodiments, the exhaust can be coupled to an exhaust bag.

In at least some embodiments, the breath sampler can further comprise a volumetric quantifier configured to indicate the volume of breath passing through the liquid capture medium in the sample collection chamber. The volumetric breath quantifier can be mechanical or based upon electrical sensors.

Advantageously, the volumetric breath quantifier can be configured to separate the breath sample into at least two sub-samples. By separating the breath sample into at least two sub-samples, a selected sub-sample of breath, e.g. from the lower respiratory tract, can be delivered to the sample collection chamber.

The volumetric breath quantifier can be further configured to selectively open a valve closing the sample outlet. For example, the breath sample may further comprise a closure member configured to selectively close the sample outlet and the volumetric breath sampler can be configured to open the closure member in response to a predetermined volume of breath passing through the volumetric breath quantifier. In some embodiments, the closure member can comprise a valve actuatable from a closed position, in which the sample outlet is blocked, to an open position, in which the sample outlet is open. The valve can be configured to be actuated after a predetermined volume of air has passed through the volumetric breath quantifier.

In at least one embodiment, the volumetric breath quantifier comprises a Geneva gear configured to deliver one or more sub-samples to the sample collection chamber. In an exemplary embodiment, the breath quantifier is positioned downstream of the outlet valve and comprises a turnstile or turnstile rotatably mounted within the breath flow pathway configured to be rotatably displaced by a defined breath volume. A geared coupling is provided between the turnstile and the Geneva gear, wherein the turnstile is configured to move the Geneva gear from a first position to a second position. Movement of the Geneva gear from the first position to the second position is configured to open the closure member to allow a second sub-sample to be delivered to the sample collection chamber.

Breath samplers according to the first aspect of the invention can comprise a plurality of selectively connectable modules. The modules can be connectable by snap fit, screw fit, push fit or other methods of assembly suitable for use in a health care setting.

Each of the selectively connectable modules can provide a different functionality. For example, a first module can comprise the non-rebreather part, comprising the first portion of the internal breath flow pathway, i.e. comprising the sample inlet, the one-way outlet valve and the one-way air inlet. A second module can comprise the second portion of the internal breath flow pathway, i.e. comprising the connection for the sample collection chamber. Further modules can be added to modify the functionality of the sampler based on patient needs.

The breath sampler can further comprise a delivery port in fluid communication with the first conduit. The delivery port be configured for connection to a nebuliser for delivering an inhaled medicament to the user. The delivery port can be integrated into the non-rebreather module or it can be provided as a separate removable module.

In some configurations, the breath sampler can comprise an integrated testing module. The integrated testing module can form part of the sample collection chamber and further comprise a lab-on-chip analyser for detecting biological or chemical markers in the sample. For example, the integrated test module can include a lateral flow immunochromatographic assay or a PCR unit with electronic detection means within a network of channels.

In addition to or as an alternative to the analyser modules incorporated into the sample collection chamber, sensors for target substances (e.g. nucleic acids, cytokines, chemokines, c-reactive protein (CRP), host and/or pathogen) can be disposed in the non-rebreather part and/or the sample delivery part. Cytokines, chemokines and CRP are known in the art and can be used as an indicator of heightened immune response in a patient. Measured levels of these substances can thus act as an indicator that a patient's impaired lung function is indeed a result of an infection. In particular, the naturally induced responses by either the host or the pathogen may be detected, which reduces or avoids the need for conversion by a pathogen.

In a second aspect of the invention, there is provided a breath sampling assembly comprising a non-rebreather part, a sample delivery part and a liquid capture part. The non-rebreather part comprises a sample inlet for connection to a mouthpiece, a one-way air inlet valve, and a one-way air outlet valve. The one-way outlet valve is in fluid communication with the liquid capture part. The liquid capture part comprises a sample collection chamber comprising a liquid capture medium and can also comprise a sample delivery tube configured to deliver the breath sample from the non-rebreather part to below the surface of the liquid capture medium. The sample delivery part provides fluid communication between the one-way outlet valve of the non-rebreather part and the sample collection chamber. The sample collection chamber can be in fluid communication with a return inlet in the sample delivery part to allow air to exit the sample collection chamber, thereby avoiding a build-up of pressure in the sample collection chamber.

Optionally, a diffuser can be provided at an open end of the sample delivery tube to split the breath sample into several streams, to increase the surface area of the sample in contact with the liquid capture medium. A sample analyser can be incorporated into or provided in fluid communication with the sample collection chamber. The sample analyser can comprise electronic detection means for target biomarkers, e.g. nucleic acids, cytokines, chemokines, CRP, hosts and/or pathogens. In particular, the sample analyser is preferably configured to detect naturally induced hosts or pathogens.

Moreover, to provide a system that can be supplied as a complete unit (including the liquid capture medium), the return outlet, with which the sample collection chamber is in communication, can comprise an air permeable, but substantially liquid impermeable boundary. For example, the return inlet can comprise micro-pores that allow the flow of air therethrough, whilst limiting or preventing the escape of liquid capture medium from the sample collection chamber.

In a third aspect of the invention, there is provided a method of collecting a breath sample from a patient. The method comprises: collecting a breath sample through a non-rebreather part comprising a sample inlet end, a one-way air inlet valve and a one-way outlet valve; delivering the collected sample through the outlet valve to a sample collection chamber; passing the sample through a sample delivery tube to a distal end of the sample delivery tube positioned below the surface of a liquid capture medium; and passing the sample through the liquid capture medium. After collection of the breath sample, the sample can be analysed immediately, or the sample can be stored for testing at a later date.

Passing the breath sample through the liquid capture medium comprises introducing the breath sample to the liquid capture medium beneath the surface of the liquid capture medium or passing the breath sample through a conduit containing the liquid capture medium. The breath sample will rise through the liquid capture medium towards the liquid surface in the form of bubbles or a stream of air, which have a surface area in contact with the liquid capture medium.

The method can further comprise the step of measuring and/or estimating the volume of breath passing through the liquid capture interface.

The method can further comprise separating the breath sample into at least two sub-samples and selectively delivering one sub-sample to the sample collection chamber. The sub-samples can be chosen by metering the volume of breath provided. A first predetermined volume can be prevented from entering the sample collection chamber, whilst a second predetermined volume can be delivered to the liquid capture medium. The first sub-sample can be chosen to correspond to breath from the lower respiratory tract, whilst the second sub-sample can be chosen to correspond to breath from the upper respiratory tract. Separate sample collection chambers can be provided to collect the first and second sub-samples respectively.

BRIEF DESCRIPTION OF THE DRAWINGS

Further features and advantages of the invention will become apparent from the description of the invention by way of non-limiting and non-exclusive embodiments. These embodiments are not to be construed as limiting the scope of protection. The person skilled in the art will realise that other alternatives and equivalent embodiments of the invention can be conceived and reduced to practice without departing from the scope of the present invention. Embodiments of the invention will be described with reference to the accompanying drawings, in which like or same reference symbols denote like, same or corresponding parts, and in which.

DETAILED DESCRIPTION OF ILLUSTRATIVE EMBODIMENTS

Figure 1:
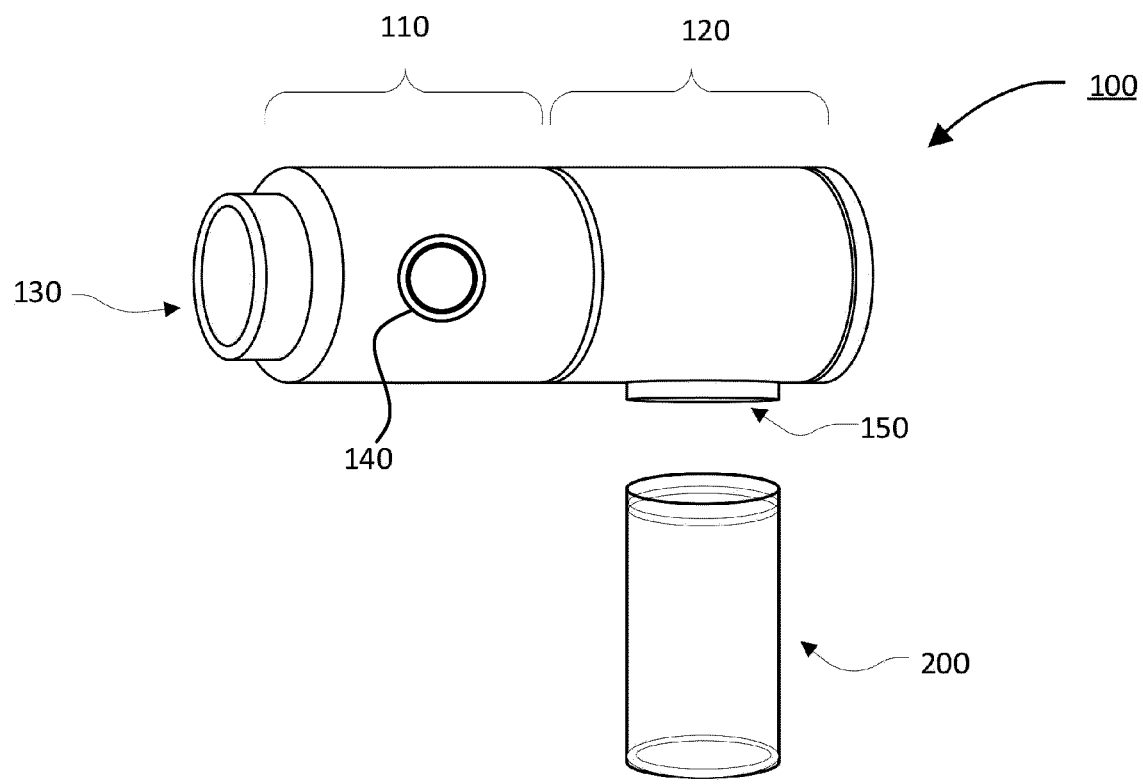
FIG. 1 shows an external side view of a breath sampler in accordance with an embodiment of the invention.

FIG. 1 shows an external view of a breath sampler in accordance with an embodiment of the invention. A breath sampler 100, comprising a non-rebreather part 110, a sample delivery part 120, a sample inlet 130, a one-way air inlet 140 and a sample collection chamber connector 150 is shown. A sample collection chamber 200 is configured for removable connection to the breath sampler 100. The sample collection chamber 200 contains a liquid capture interface (a liquid medium through which the breath sample is passed to capture chemical and/or biological markers from the exhaled breath), which can subsequently be tested.

By providing a liquid capture interface, more consistent and more sensitive samples can be collected for analysis. Due to the non-rebreather part, the patient can breathe normally throughout the sampling process without inhaling the contents of the sample collection chamber 200. This may be particularly important for patients with impaired lung function, who often find providing a sample of sputum or breath challenging, when using known methods.

Figure 2:
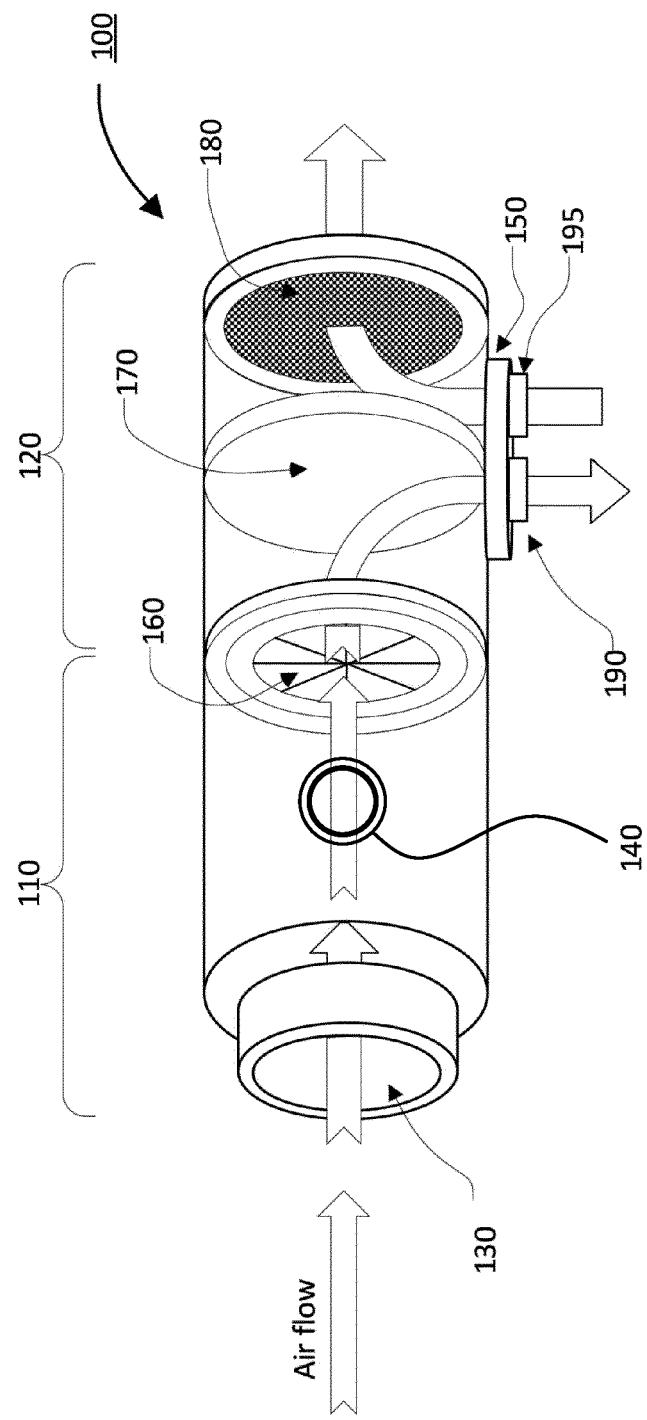
FIG. 2 shows an internal breath flow pathway through a breath sampler.

Referring now to FIG. 2, breath sampler 100 comprises a non-rebreather part 110, which defines a first portion of a breath flow pathway. The non-rebreather part 110 extends from the sample inlet 130 at an upstream end, to a one-way outlet valve 160 at a downstream end. The sample inlet 130 may be directly used as a mouthpiece, or may facilitate connections to a specialised mouthpiece, (e.g. a breathing mask or in-mouth mouthpiece), for example by means of a universal connector. The one-way outlet valve 160 is configured to allow air to exit the non-rebreather part 110 through the valve 160 in a downstream direction, whilst preventing the flow of air into the non-rebreather part 110 through the outlet valve 160 (in an upstream direction). In some embodiments, outlet valve 160 and/or air inlet 140 comprises a silicone valve.

An air inlet 140, which is closed by a one-way inlet valve, is provided between the sample inlet 130 and the one-way outlet valve 160. The one-way inlet valve may comprise a silicone valve. The air inlet 140 is configured to allow air to flow into the non-rebreather part 110 through the one-way inlet valve, whilst preventing the flow of air out of the non-rebreather part 110 through the one-way inlet valve. In the embodiment shown in FIGS. 1 and 2, the air inlet 140 is positioned on a side of the breath sampler's non-rebreather part 110, in an in-use orientation (with the sample collection chamber 200 extending from a lower surface of the device such that the liquid capture medium 310 pools at the distal end of the sample collection chamber 200). Positioning the air inlet 140 on one side of the device is particularly suitable for hospital use, because this placement allows the connection of a nebuliser module on the lower side of the first conduit 110 (discussed in more detail with reference to FIGS. 5A and 5B). Moreover, as patients have a tendency to hold the device with a finger placed over the upper surface of the device during use, orienting the air inlet 140 on the side of the breath sampler minimises the risk that the patient inadvertently blocks the air inlet 140. Although the positioning of air inlet 140 on the side of the device is advantageous, the skilled person will recognise that the air inlet 140 can be positioned at other points on the breath sampler device, as shown through the enclosed figures.

Although depicted in FIG. 2 as a circular valve, other shapes and configurations of air inlet 140 are also suitable. For example, air inlet 140 may additionally or alternatively comprise a plurality of slits at one or more positions along the exterior of the breath sampler.

The combination of the one-way inlet and outlet valves (e.g. air inlet 140 and outlet valve 160, respectively) provides a non-rebreather part through which a user can breathe normally (in and out), without inhaling all or part of the collected sample. During an inhalation by the user, the user continues to breathe with the mouthpiece (not shown). Air enters the breath sampler 100 via air inlet 140 and continues to the user via the mouthpiece. During exhalation, the air inlet 140 is closed, forcing the exhaled breath along the internal breath flow pathway (i.e. into the second portion of the internal breath flow pathway).

The sample delivery part 120 is configured for connection to a sample collection chamber 200 (as shown in FIG. 1) which comprises a liquid capture interface. The sample delivery part 120 comprises an upstream end configured to receive air from the one-way outlet valve 160 and an air diverter 170 that is configured to direct the flow of air through a sample outlet 190 into the sample collection chamber 200 and to the liquid capture interface. A connector 150 is provided to couple the sample collection chamber 200 to the sample delivery part. The connector 150 can comprise e.g. a push fit, screw fit or bayonet attachment for a sample collection chamber containing a liquid capture interface. Other connector assemblies that provide a seal between the sample delivery part 120 and the sample connection chamber 200 will be apparent to the person skilled in the art.

The connector 150 defines a perimeter at the point at which it forms a seal with the sample collection chamber 200. With the perimeter defined by the connector 150, the sample delivery part 120 comprises a sample outlet 190 and a return opening 195.

The air diverter 170 is positioned between the sample outlet 190 and the return opening (or return inlet) 195 and is configured to fluidically separate the sample delivery part 120 into an upstream portion and a downstream portion. The sample outlet 190 is disposed upstream of the air diverter 170, whilst the return opening 195 is disposed downstream of the air diverter (and in fluid communication with the exhaust 180. The exhaust can be covered with a mesh or bacterial filter, or it can be left open.

In some embodiments, exhaust 180 may be covered with a sampler cap (not shown). The sampler cap may protect the exhaust 180 during shipping and transport, and, in some embodiment, should be removed prior to use of the breath sampler apparatus. In some embodiments, however, the sampler cap comprises a series of gaps or holes, enabling the breath sampler to be used whilst the sampler cap is attached. The sampler cap may, in these cases, provide support and/or structure to the exhaust. The sampler cap may act as a support housing for a filter or mesh, if either a filter or a mesh is provided. The sampler cap may protect a filter or mesh, especially during shipping when damage is more likely to occur. Additionally, the filter or mesh may benefit from a support housing during use. The sampler cap may be attached by a push fit, screw fit, or bayonet attachment, or the like.

In some embodiments, exhaust 180 is provided on a side wall of the breath sampler, for example as a plurality of one-way slits. For example, the end of the breath sampler (corresponding to the position of exhaust 180 in FIG. 2) may be closed, for example by a removable cap (not shown). In an example, the end of the breath sampler 100 is sealed by a sampler-and-chamber cap and the exhaust 180 is disposed along a wall of the breath sampler, downstream of the air diverter 170. After a sample has been collected, the sampler-and-chamber cap may be removed from the end of the breath sampler 100 and attached to the sample collection chamber 200 to seal the used sample collection chamber 200. The provision of the sample-and-chamber cap in this way enables the breath sampler device to be delivered to a patient pre-assembled with a sample collection chamber, and allows the patient to remove and close the sample collection chamber after use, such that it may be transported or shipped for analysis. In this way, patient assembly is simplified whilst ensuring that the captured breath sample may be reliably transported.

In other words, in some embodiments, the breath sampler 100 may further comprise a breath sampler cap configured to removably attach to a distal end of the breath sampler 100, the distal end of the breath sampler 100 being an end opposite to an end comprising the sample inlet 130. The sampler cap may be arranged to cover the exhaust 180. Additionally or alternatively, the sampler cap may comprise connection means corresponding to the sample collection chamber 200.

Figure 3:
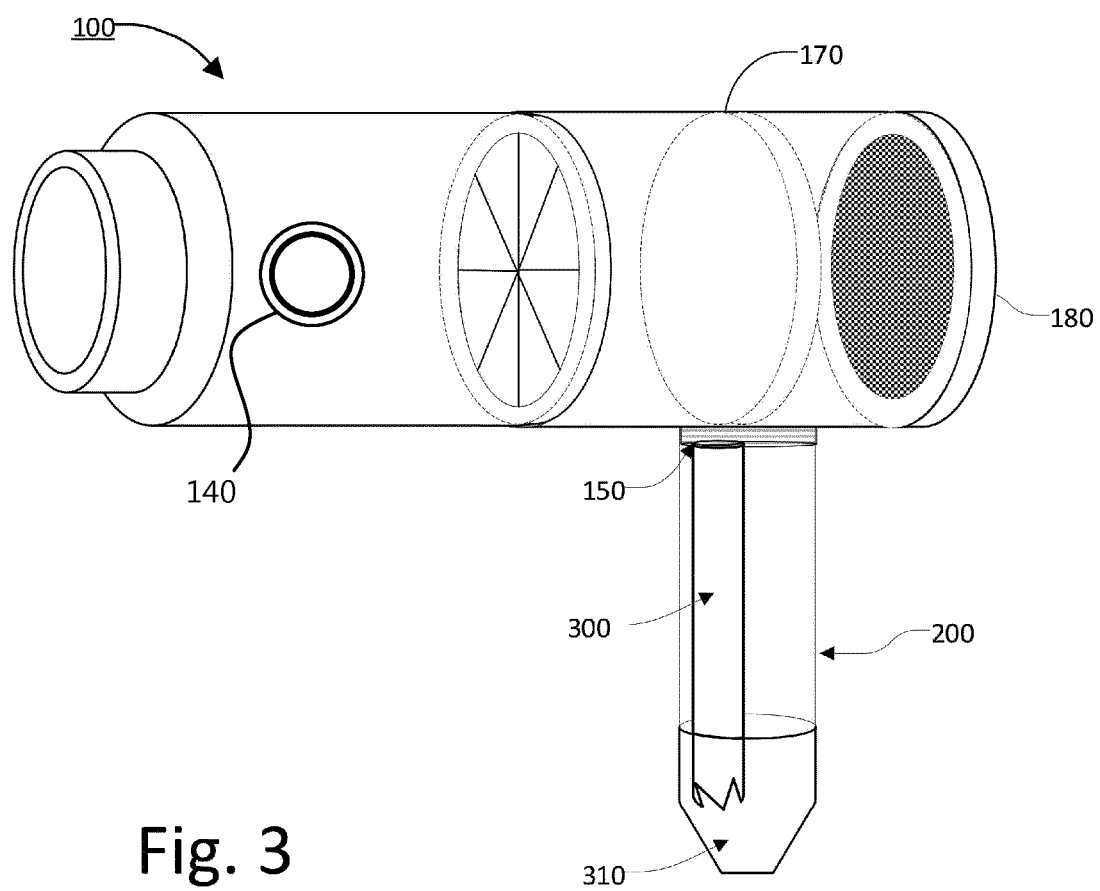
FIG. 3 shows an embodiment of a breath sampler comprising a sample collection chamber.

Turning now to FIG. 3, a sampling assembly comprising the breath sampler 100 and the sample collection chamber 200 will be described.

As shown in FIG. 3, the sample collection chamber 200, also referred to as a chamber, a vial or a sample tube, provides a reservoir for a liquid capture medium 310, and is configured for connection to the connector 150 at an open end. The connection with connector 150 can be by means of threaded engagement, push- or snap-fit engagement, or other connecting means that will be apparent to the person skilled in the art.

The sample collection chamber 200 can comprise a standard 50 mL laboratory tube, suitable for use in many standard laboratory apparatuses (e.g. a centrifuge). However, the skilled person will appreciate that other sample collection chamber configurations are possible. The skilled person will recognise that the volume of the chamber 200 (and the volume of the liquid capture medium 310 within the chamber 200) can be selected depending on the volume of sample required for analysis. For example, a sample intended for lab-on-chip PCR analysis requires a small volume of liquid sample (e.g. less than 0.5 mL). However, where multiple analyses are planned, for example, conventional culturing techniques and a rapid analysis, larger volumes of sample will generally be required.

In some embodiments, a sample collection chamber adapter (not shown) may be provided. The sample collection chamber adapter can be an adapter allowing a standard tube or chamber (or similarly, one of a plurality of standard tubes or chambers) to connect to the sample collection chamber connector 150 of the breath sampler 100, thereby improving compatibility with existing tubes and/or receptacles, such as those commonly used in health care services.

The liquid capture medium 310 can be chosen depending on the analysis technique for which the sample is to be captured. For example, the liquid capture medium can be a salt solution (e.g. a phosphate buffered salt solution), a culture medium (e.g. a tryptic soy broth) or water for injection. In at least some embodiments, a particle collection substrate can be disposed within the liquid capture medium, configured to entrain particles (e.g. pathogens) of interest.

The volume of liquid capture medium 310 can also vary depending on the analysis technique to be used. The volume of liquid disposed within the sample collection chamber 200 is preferably between 0.1 ml and 10 ml, and more preferably between 0.5 ml and 2.5 ml.

To deliver the breath sample from the sample delivery part 120 to the sample collection chamber 200 and the liquid interface, a sample delivery tube 300 is connected to (or integrally attached to) the sample outlet 190. The sample delivery tube 300 extends from a proximal end connected to the outlet 190 to an open distal end that is configured to be disposed below the surface of the liquid capture medium 310. The precise configuration of the sample delivery tube 300 at the positioning of its distal end can be varied depending on the dimensions of the sample collection chamber 200 and on the volume of liquid capture medium disposed within the chamber 200. However, it is preferred that the open end of the sample delivery tube 300 (or a diffuser, where used) is disposed within a distal half of the sample collection chamber, more preferably a distal quarter, more preferably adjacent the distal end of the sample collection chamber 200.

During use, breath from the patient passes through the non-rebreather part 110, and is delivered via the sample delivery part 120 to the sample outlet 190. From the sample outlet 190, the breath sample passes through tube 300 and escapes from the open distal end of the sample delivery tube 300 below the surface of the liquid capture medium. The breath sample passes through the liquid capture medium, in which chemical and/or biological markers (e.g. pathogens) are captured. The liquid capture medium can then be analysed (as discussed in further detail below) for diagnostic purposes.

To prevent the build-up of pressure in the sample collection chamber, the sample delivery part 120 comprises a return inlet 195, which is configured to be in fluid communication with the internal volume of the sample collection chamber 200. In the embodiment shown in FIGS. 2 and 3, the return inlet 195 is disposed within the perimeter of the connector 150, downstream of the air diverter 170, and in fluid communication with the exhaust 180.

The non-rebreather part 110 will now be described in more detail with reference to FIGS. 4A-5B.

Figure 4A:
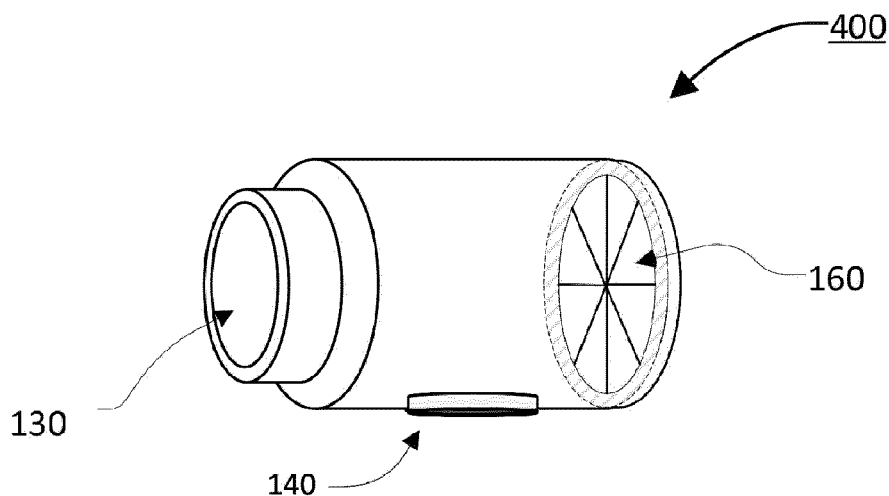
FIG. 4A shows a top view of a first module corresponding to a non-rebreather part of a breath sampler according to an embodiment of the invention.
Figure 4B:
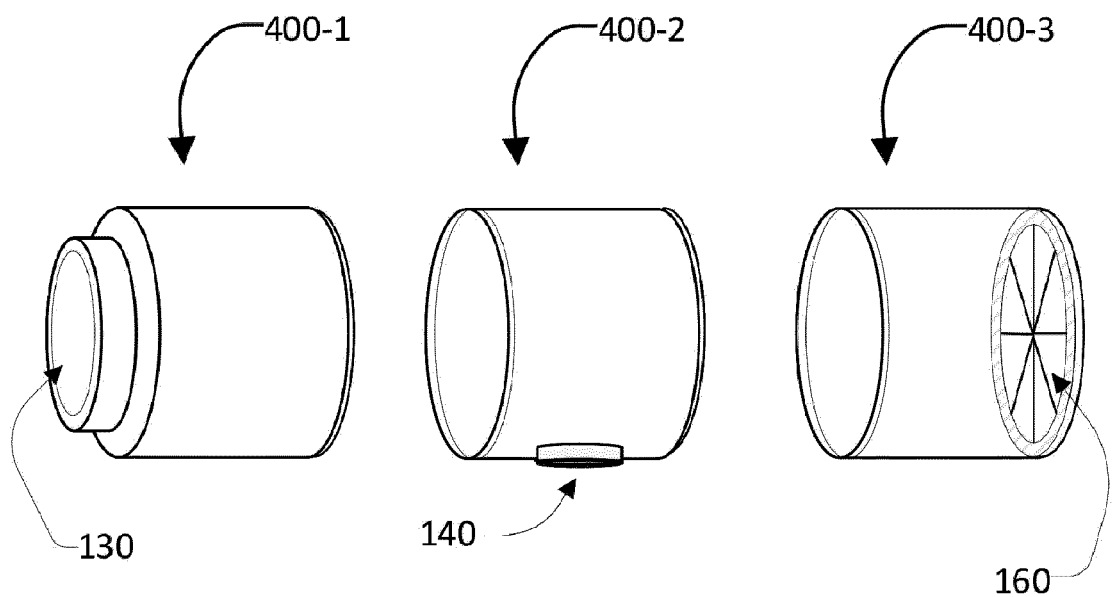
FIG. 4B shows a top view of an alternative modular composition corresponding to a non-rebreather part of a breath sampler according to an embodiment of the invention.

FIGS. 4A and 4B show a top view of non-rebreather part 110. As shown in FIGS. 4A and 4B, the non-rebreather part 110 can comprise a single component 400, or a series of interconnected pieces 400-1, 400-2, 400-3. A plurality of interconnectable pieces allows characteristics of a non-rebreather module to be varied independently.

Referring first to FIG. 4A, a first module 400 comprising sample inlet end 130, air inlet 140 and one-way outlet valve 160 is shown. First module 400 corresponds to non-rebreather part 110 shown in FIGS. 1 and 2. The first portion of the internal breath flow pathway occurs within first module 400. In FIG. 4A, the sample inlet end 130, air inlet 140 and one-way outlet valve 160 are all disposed on a single modular component. There exist, however, alternative configurations in which these components are disposed on separate connectable modules, as illustrated in FIG. 4B.

Referring now to FIG. 4B, module 400 of FIG. 4A comprises separable and connectable sub-modules 400-1, 400-2 and 400-3. Sub-module 400-1 comprises sample inlet end 130, whilst sub-module 400-2 comprises air inlet 140 and sub-module 400-3 comprises one-way outlet valve 160. The modular structure shown in FIG. 4B can be particularly beneficial in certain situations and use-cases, as it can operate as a universal connector, enabling known and future mouthpieces to be fitted to the breath sampler 100. The breath sampler 100 can be easily configured based on the needs of a test, treatment, or diagnosis. Furthermore, maintenance and cleaning can be simplified through such a modular construction.

Although not depicted, the skilled person will readily appreciate that further constructions are possible. For example, sample inlet end 130 and air inlet 140 may be disposed on a single modular component with one-way outlet valve 160 being disposed on another modular component, or sample inlet end 130 may be disposed on a single modular component with air inlet 140 and one-way outlet valve 160 both being disposed on a single other modular component.

In some embodiments, first module 400 may be further equipped with a delivery port, which may be used to connect a nebuliser or similar breathing aide.

Figure 5A:
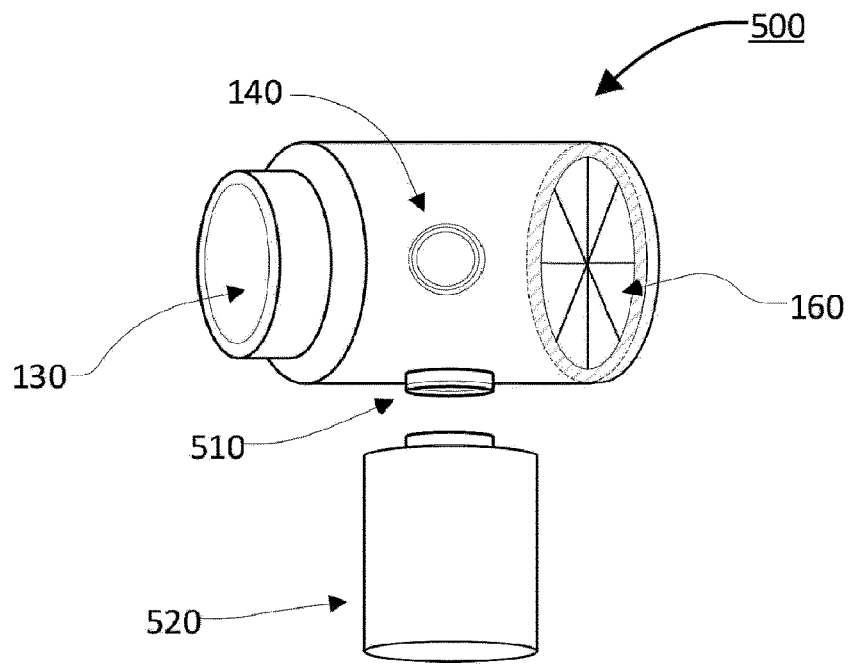
FIG. 5A and FIG. 5B show a side view of a modified first module additionally comprising a second input valve.
Figure 5B:
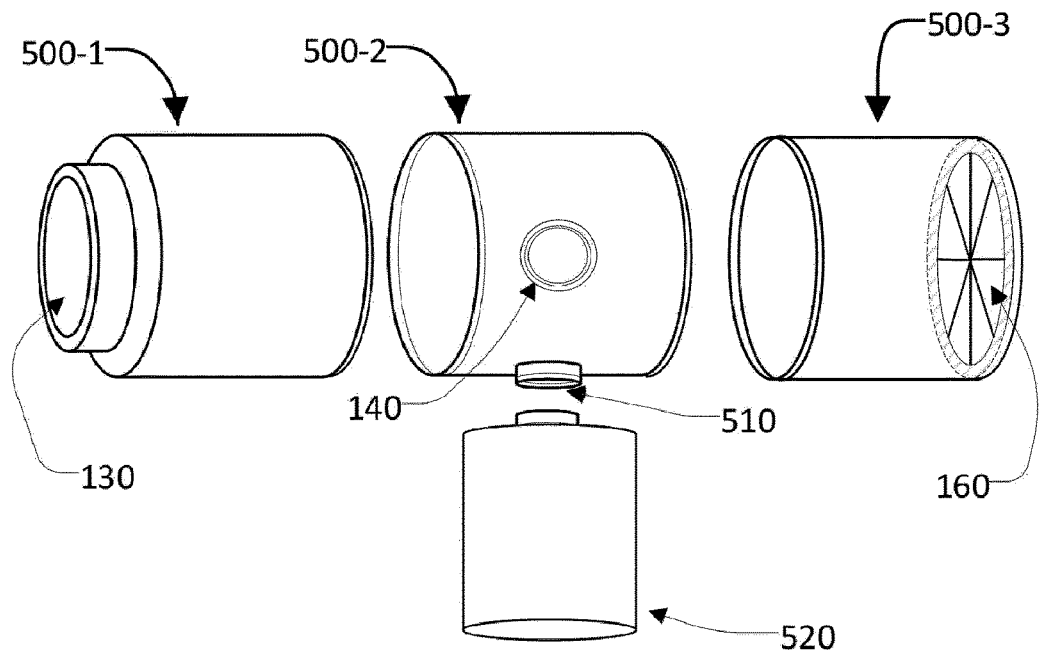

FIG. 5A and FIG. 5B show a modified first module additionally comprising a delivery port. Referring to FIG. 5A, first module 500 is illustrated. First module 500 corresponds to first module 400 of FIG. 4A, with the addition of delivery port 510. Delivery port 510 facilitates a connection of a nebuliser, such as nebuliser 520, or similar breathing aide, and enables the delivery of medication such as bronchodilators. The port 510 can comprise a one-way valve configured to allow fluid flow (air or liquid) into the first conduit 110, whilst preventing flow in the opposite direction.

FIG. 5B illustrates an alternative modular construction of first module 500, in which first module 500 comprises separable and connectable sub-modules 500-1, 500-2 and 500-3, as described in relation to FIG. 4B with the addition of delivery port 510. Delivery port 510 is illustrated as being disposed on sub-module 500-2, the same modular component upon which air inlet 140 is disposed, however other constructions are considered. For example, delivery port 510 may be disposed on a fourth sub-module (not shown) between sub-module 500-1 and sub-module 500-2, or between sub-module 500-2 and sub-module 500-3. As another example, delivery port 510 may be disposed on one of sub-modules 500-1 and 500-3. Similarly to the example of FIG. 4B, the modular construction may be in a different form, with different components either alone or in combination on different modular components. For example, sample inlet end 130, delivery port 510 and air inlet 140 may be disposed on a single sub-module with one-way outlet valve 160 being disposed on another sub-module, or sample inlet end 130 and air inlet 140 may be disposed on a sub-module, delivery port 510 being disposed on another sub-module and one-way outlet valve 160 being disposed on yet another sub-module. It can be readily understood that further combinations are possible, such that air inlet 140 and delivery port 510 are disposed between sample inlet end 130 and one-way outlet valve 160 when assembled.

Figure 6A:
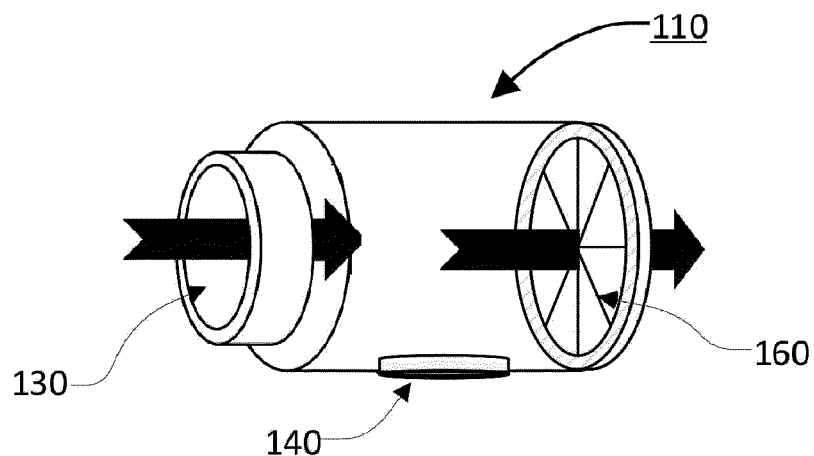
FIGS. 6A and 6B show a top view of a first module operating as a non-rebreather module.

The flow of air through the non-rebreather part 110 during normal breathing (in and out) is illustrated by FIGS. 6A to 6D. As shown in FIG. 6A, during an exhalation, breath flows from the patient's lungs through the sample inlet 130 into the non-rebreather part 110. Since the one-way air inlet valve 140 does not allow air to flow in an outward direction, the breath flows along the non-rebreather part 110 and through the one-way outlet valve 160, towards the sample delivery part 120.

Figure 6B:
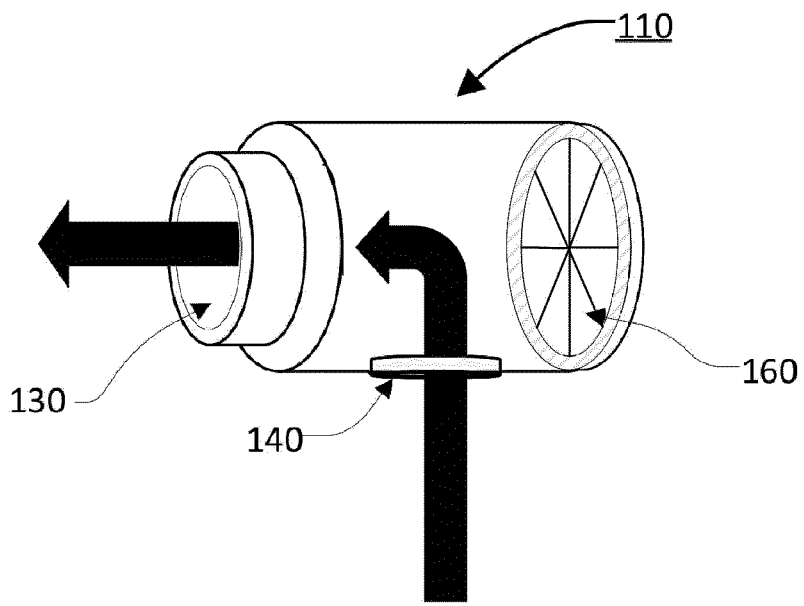

Referring now to FIG. 6B, during an inhalation, air flows into the non-rebreather part 110 through the air inlet 140 and into the patient's lungs via the sample inlet 130. Since the one-way outlet valve 160 prevents air flow therethrough in an upstream direction (into the non-rebreather part 110), the patient does not inhale any air or fluid downstream of the one-way outlet valve 160.

Figure 6C:
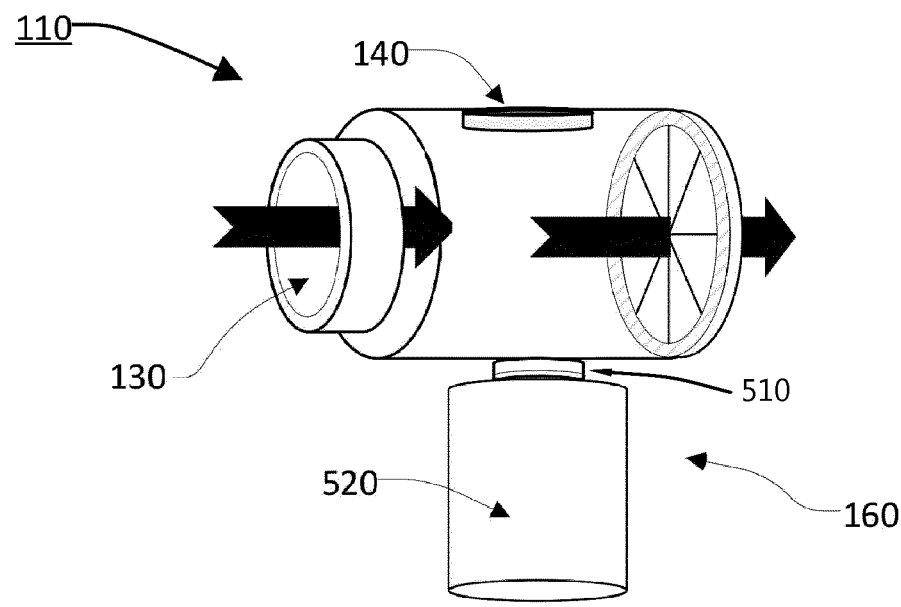
FIGS. 6C and 6D show a side view of a first module operating as a non-rebreather module in an embodiment further comprising a delivery port for connecting a nebuliser.
Figure 6D:
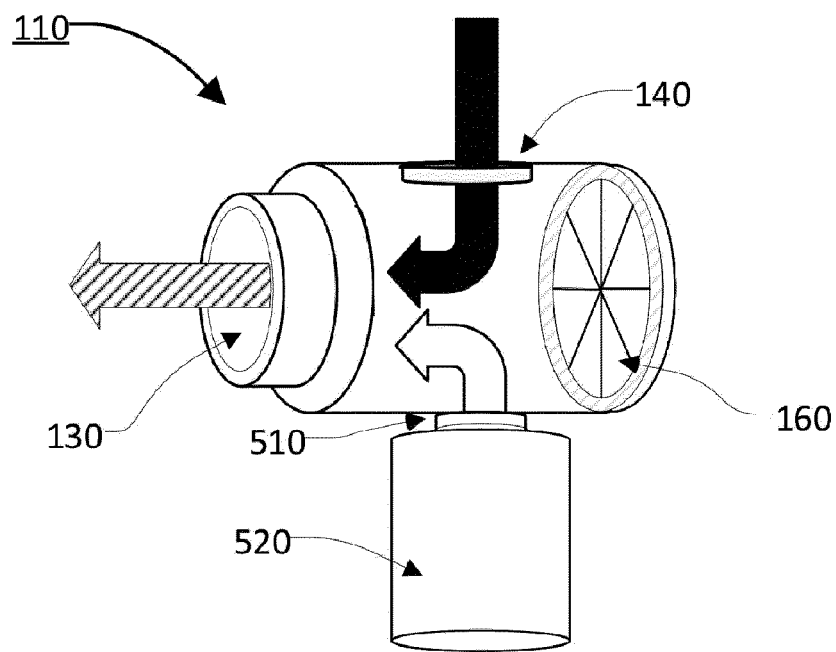

FIGS. 6B and 6C show the flow of air through the non-rebreather part 110, where a medicament is delivered through the delivery port 510. As shown in FIG. 6C, during an exhalation, the breath flows through the one-way outlet valve 160, with one-way valves preventing the flow of the air inlet and the delivery port 510. As shown in FIG. 6D, during an inhalation, air is drawn in though the air inlet 140 and through the delivery port 510. Medicament (e.g. a broncho-dilating substance) is therefore breathed in by the patient to assist the sampling process.

Figure 6E:
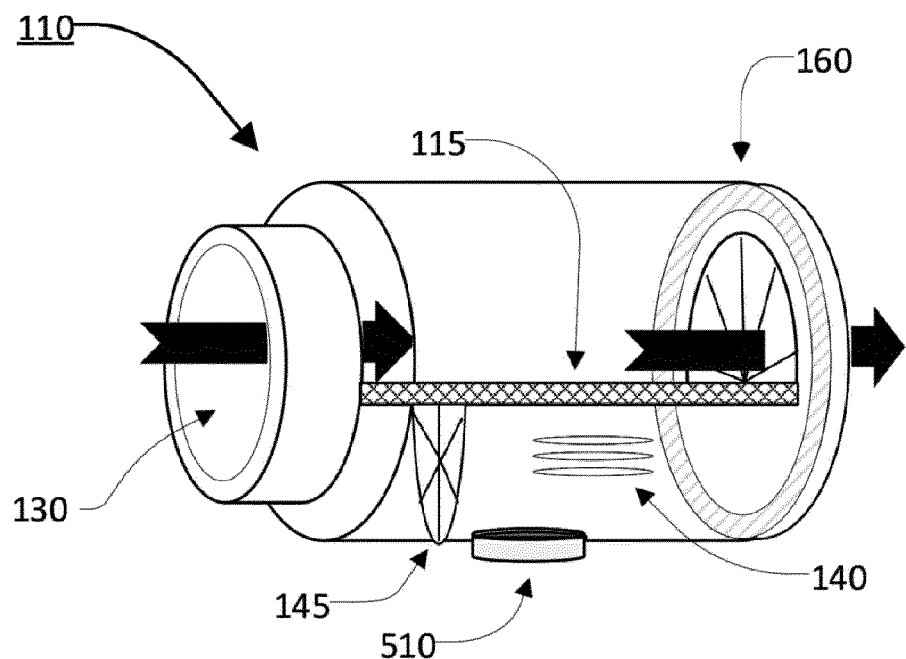
FIGS. 6E and 6F show an alternative configuration of a non-rebreather part according to an embodiment of the invention.
Figure 6F:
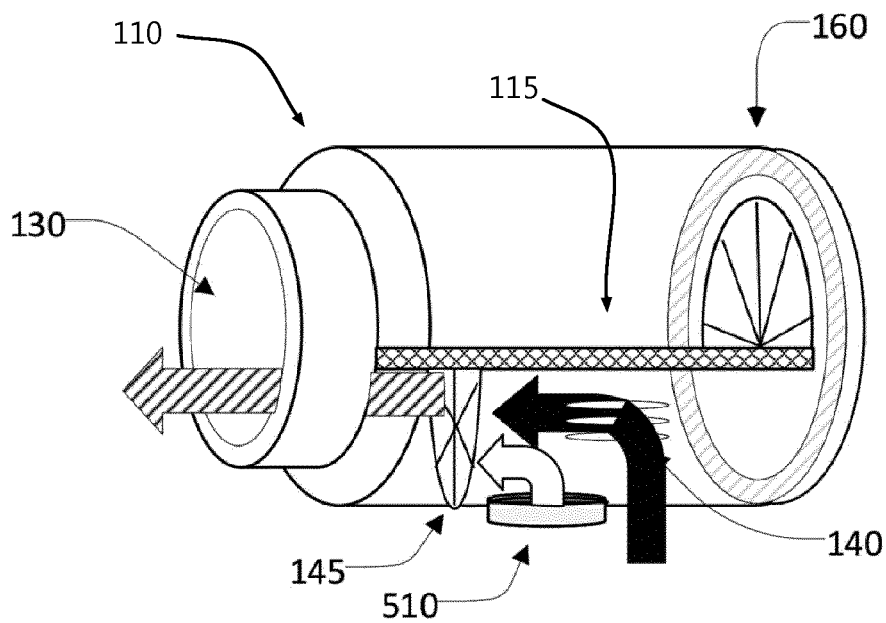

Note that in the representation shown in FIGS. 6C and 6D, the air inlet 140 is depicted on the top side of the breath sampler. This placement of the air inlet 140 is chosen merely to allow an unhindered view of the schematic air flow through the device. However, the skilled person will understand that the position of the air inlet 140 can be modified as necessary. Additionally or alternatively, the air inlet 140 may be configured as a plurality of slits in one or more positions along the wall of the breath sampler, within the non-rebreather part 110. FIGS. 6E and 6F show an alternative configuration of a non-rebreather part according to an embodiment of the invention.

Referring to FIGS. 6E and 6F, according to an embodiment of the present invention, the non-rebreather part 110 is provided with an alternate configuration. The non-rebreather part 110 of FIGS. 6E and 6F comprises a dividing wall 115, which divides the non-rebreather part 110 into an inhalation region and an exhalation region. During exhalation, a breath sample enters the exhalation region of the non-rebreather part 110 and continues through one-way outlet valve 160. This is illustrated by black arrows in FIG. 6E.

Optionally, the air inlet 140 may comprise a plurality of slits in the wall of the breath sampler 100, as shown in FIGS. 6E and 6F. Additionally, an optional delivery port 510 may be provided in order to enable a nebuliser, such as nebuliser 520, to be connected. As illustrated in FIGS. 6E and 6F, exhaled air may be prevented from escaping through delivery port 510 and/or air inlet 140 by means of a one-way air inlet valve 145. The provision of one-way air inlet valve 145 upstream of the air inlet 140 and, if present, the delivery port 510, may simplify the construction of the device. Additionally, air inlet 140 may comprise slits in various positions around the wall of the breath sampler 100. Thus it may be advantageous to provide a single one-way valve such as one-way air inlet valve 145. It is noted that although the one-way outlet valve 160 is shown further away from the mouthpiece than the air inlet valve 145, the invention is not limited thereto. In some embodiments, the one-way outlet valve 160 is positioned in alignment with the air inlet valve 145 (i.e. such that the distance between the mouthpiece and the air inlet valve 145 is equal to (or similar to) the distance between the mouthpiece and the one-way outlet valve 160, the one-way outlet valve 160 and the air inlet valve 145 being on different sides of the dividing wall 115). In still other embodiments, the distance between the air inlet valve 145 is further away from the mouthpiece than the one-way outlet valve 160.

During inhalation, one-way outlet valve 160 prevents the patient from inhaling already-sampled breath and/or liquid from the liquid capture interface. One-way air inlet valve 145 enables air to flow from outside the breath sampler 100 into the inhalation region of the non-rebreather part 110 via air inlet 140 and, optionally, delivery port 510.

The sample delivery part 120 will now be described in more detail with reference to FIGS. 7A to 9B.

Figure 7A:
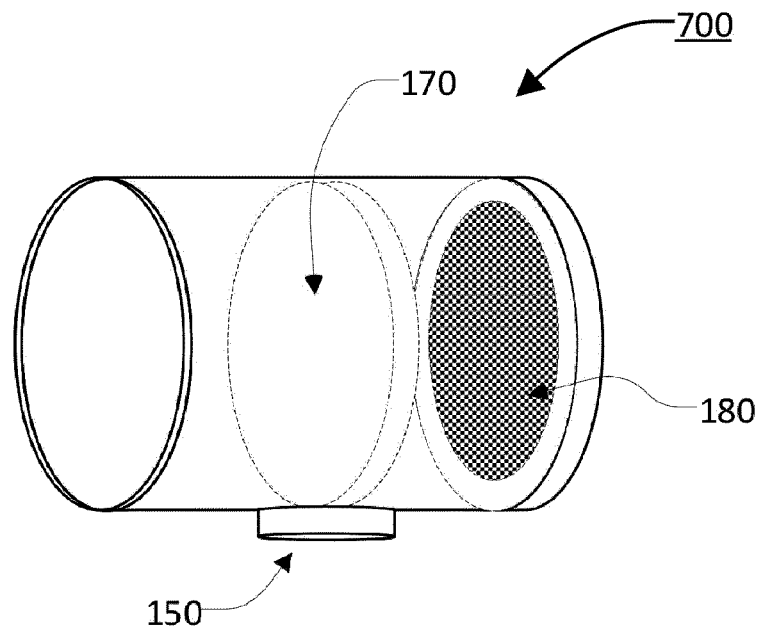
FIG. 7A shows a second module corresponding to a sample delivery part of a breath sampler according to an embodiment of the invention.

FIG. 7A shows the sample delivery part 120 of the breath sampler 100. As shown in FIG. 7A, the sample delivery part 120 extends from an upstream end configured for attachment in fluid communication with the outlet valve 160 of the non-rebreather part 110 to a downstream end comprising an exhaust 180. The upstream end of the sample delivery part 120 can be configured for direct attachment to the non-rebreather part 110 (as shown in FIG. 1) or it can be configured to be fluidically connected to the non-rebreather part 120 via an intermediate component (discussed in further detail with reference to FIG. 10). The connection with the non-rebreather part 110 can be via a threaded engagement, push- or snap-fit engagement, or other engagement means that will be apparent to the person skilled in the art in light of the present disclosure. Sealing components, such as O-rings or other seals, can be provided to ensure a substantially airtight connection between the non-rebreather part 110 and the sample delivery part 120.

The sample delivery part 120 is divided into two fluidically separated portions by the air diverter 170. As shown in FIG. 7A, the air diverter 170 comprises a wall that prevents the direct flow of air from the upstream end of the sample delivery part 120 to the exhaust 180. The air diverter 170 is preferably impermeable to gas and liquid such that air cannot flow through the air diverter to the downstream portion of the sample delivery part 120.

The purpose of the air diverter 170 is to divert air from the sample delivery part into the sample collection chamber 200. Therefore, the sample delivery part comprises a sample outlet 190 upstream of the air diverter 170 through which air can exit the sample delivery part 120 and enter the sample collection chamber 200. Air is able to re-enter the sample delivery part 120 downstream of the air diverter 170 via return inlet 195 and thereafter escape from the breath sampler 100 via exhaust 180.

Figure 7B:
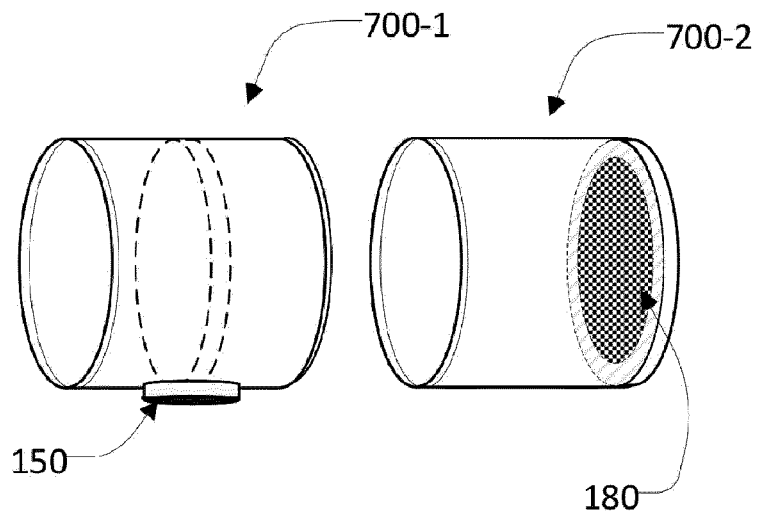
FIG. 7B shows an alternative modular composition corresponding to a sample delivery part of a breath sampler according to an embodiment of the invention.

As shown in FIG. 7A, the sample delivery part 120 can be provided as a single module 700 or it can comprise a plurality of interconnectable modules 700-1, 700-2, as shown in FIG. 7B.

In FIG. 7B, the sample delivery part 120 is provided as a plurality of interconnectable modules 700-1 and 700-2. Sub-module 700-1 can comprise the air diverter 170 and the sample collection chamber connection 150, and sub-module 700-2 can comprise the exhaust 180. Sub-module 700-1 may connect to sub-module 700-2 during use, or there may be further sub-modules disposed therebetween.

Figure 8A:
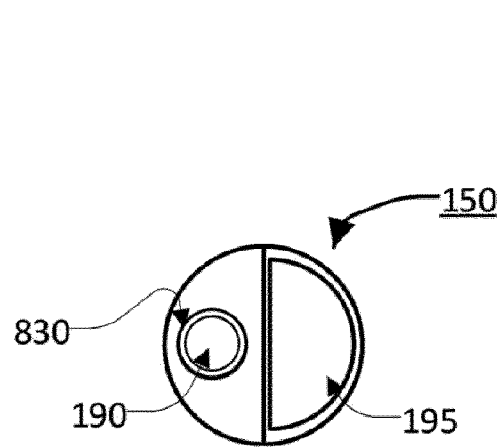
FIG. 8A shows an exemplary sample outlet.
Figure 8C:
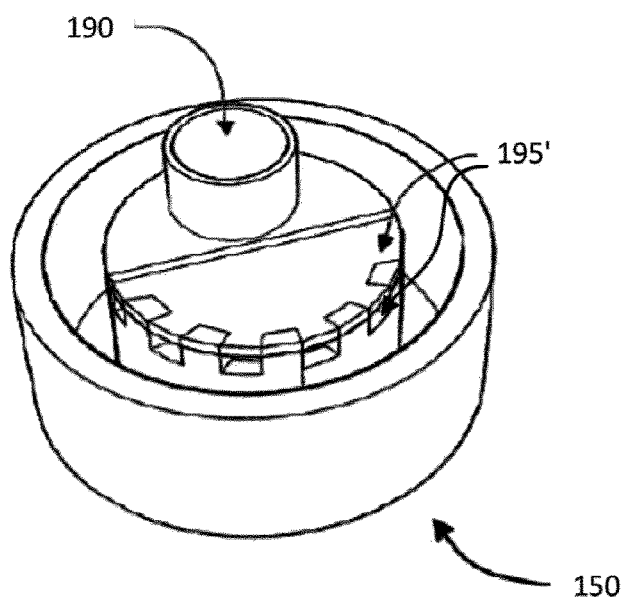
FIG. 8C shows a sample collection assembly comprising an amalgamator.
Figure 8B:
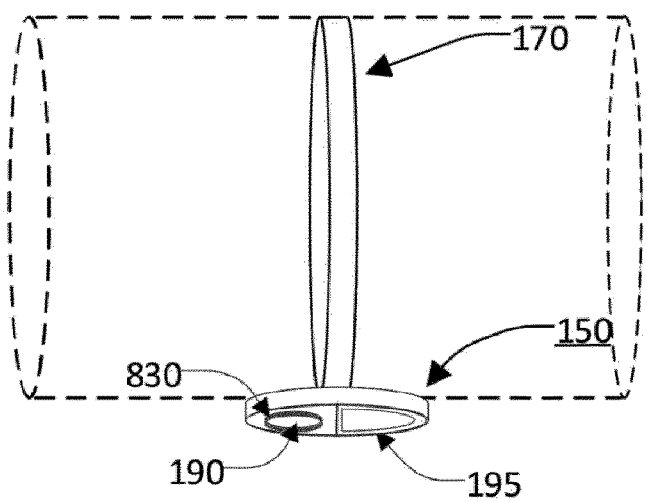
FIG. 8B shows a schematic view of an air diverter in alignment with a sample collection connection assembly.

FIGS. 8A to 8C show the sample collection chamber connector 150, the sample outlet 190 and the return inlet 195 in more detail. As shown in FIG. 8A, the connector 150 defines a perimeter P that forms a seal with the sample connection chamber 200. The connector 150 can comprise threaded engagement means, a push- or snap-fit connector or other connection means that will be apparent to the person skilled in the art.

As shown in FIG. 8A, the sample outlet 190 and the return inlet 195 are disposed within the perimeter P defined by the sample collection chamber connector 150. This allows air to exit and re-enter the sample delivery part 120 via the sample collection chamber 200 through the sample outlet 190 and the return inlet 195, respectively. As shown in FIG. 8A, the sample outlet 190 can comprise an aperture configured to receive a length of flexible tube, such as sample delivery tube 300. The sample outlet 190 can comprise a neck or collar 830 over which a flexible length of tube (such as sample delivery tube 300) can be pressed. Alternatively, the sample outlet 190 can comprise an integrated sample delivery tube 300. The sample delivery tube 300 delivers the breath sample to the liquid capture medium 310 (shown in FIG. 3).

Since the return inlet 195 is disposed within the perimeter of the connector 150, the return inlet 195 is in fluid communication with the interior volume of the sample collection chamber 200. Thus, the return inlet 195 allows air from the sample collection chamber 200 to return to the sample delivery part 120 and ultimately escape through the exhaust 180. The air diverter 170 extends between the sample outlet 190 and the return inlet 195. This prevents the air from bypassing the sample collection chamber 200 and forces the breath sample to enter the chamber 200 for liquid capture of particles of interest. The positioning of the air diverter 170 relative to the sample outlet 190 and the return inlet 195 is further illustrated in the side view shown in FIG. 8B.

FIG. 8C shows a preferred embodiment of the connector 150 according to the present invention. As shown in FIG. 8C, the connector 150 can comprises an outer collar to which the sample collection chamber 200 is attached. This attachment can be by means of a screw thread, snap-fit or other suitable connection types. Disposed within the collar is a projection, on which is mounted the sample outlet 190. However, instead of a single return opening as shown in FIG. 8A, in the embodiment shown in FIG. 8C, the return opening takes the form of a plurality of openings or pores 195' disposed on the projection. The pores or openings 195' are preferably sized to allow the passage of air therethrough (to prevent excessive pressure build up in the sample collection chamber) but to prevent the passage of liquid droplets. The plurality of holes can optionally be provided on a side portion of the projection (opposite the collar) such that a droplet following a trajectory directly towards the outlet cannot fly through the openings or pores 195'. The openings or pores 195' open into the downstream portion of the sample delivery part 120, such that the plurality of airstreams passing through the pores 195' can converge before exiting the device through the exhaust. The arrangement of components shown in FIG. 8C is collectively referred to as an amalgamator. Any of the embodiments described herein may be adapted to use the amalgamator arrangement of FIG. 8C without the need for further modifications.

Figure 9A:
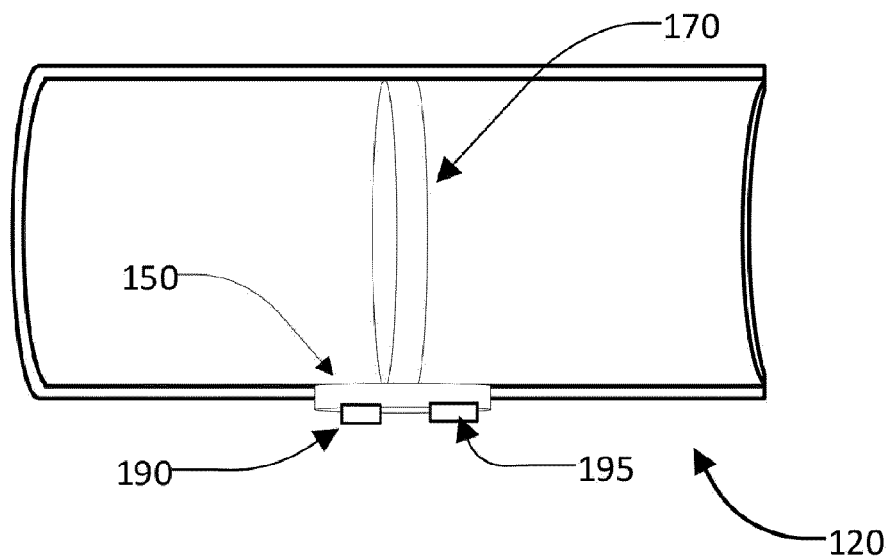
FIGS. 9A and 9B show two different exemplary configurations of an air diverter.
Figure 9B:
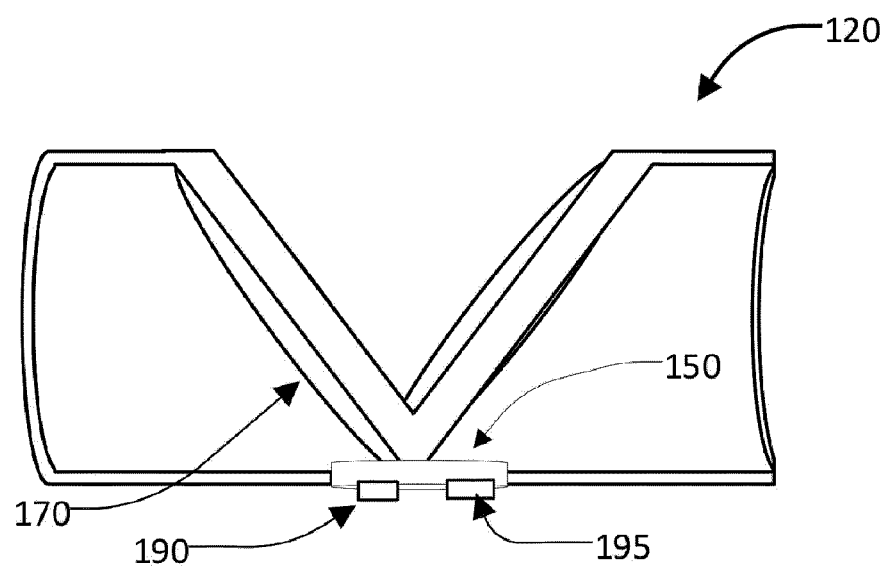

Turning now to FIGS. 9A and 9B, the air diverter can be configured in different ways. For example, as shown in FIG. 9A, the air diverter can comprise a wall extending in a plane that is substantially perpendicular to the longitudinal axis of the sample delivery part 120. Alternatively, as shown in FIG. 9B, the wall can comprise a notch in the sample delivery part 120 that prevents the direct flow of breath from the upstream end to the exhaust 180 (without passing through the sample collection chamber 200). The skilled person will appreciate that other configurations are possible, and the air diverter can comprise alternative wall configurations, or a network of channels that deliver the breath sample from the one-way outlet valve 160 to the exhaust 180 via a liquid capture sample collection chamber 200.

In other words, the air diverter 170 divides the sample delivery part 120 into two portions: an upstream portion between the diverter 170 and the one-way outlet valve; and a downstream portion between the diverter 170 and the exhaust 180. The air diverter 170 can take the form of a wall that fluidically separates the upstream portion from the downstream portion. It can extend in a plane that is perpendicular to a longitudinal axis of the sample delivery part 120, or at a non-perpendicular transverse angle. The skilled person will appreciate that the air diverter 170 can take many forms and different structural arrangements can be used to separate the sample delivery part 120 into upstream and downstream portions.

Figure 10A:
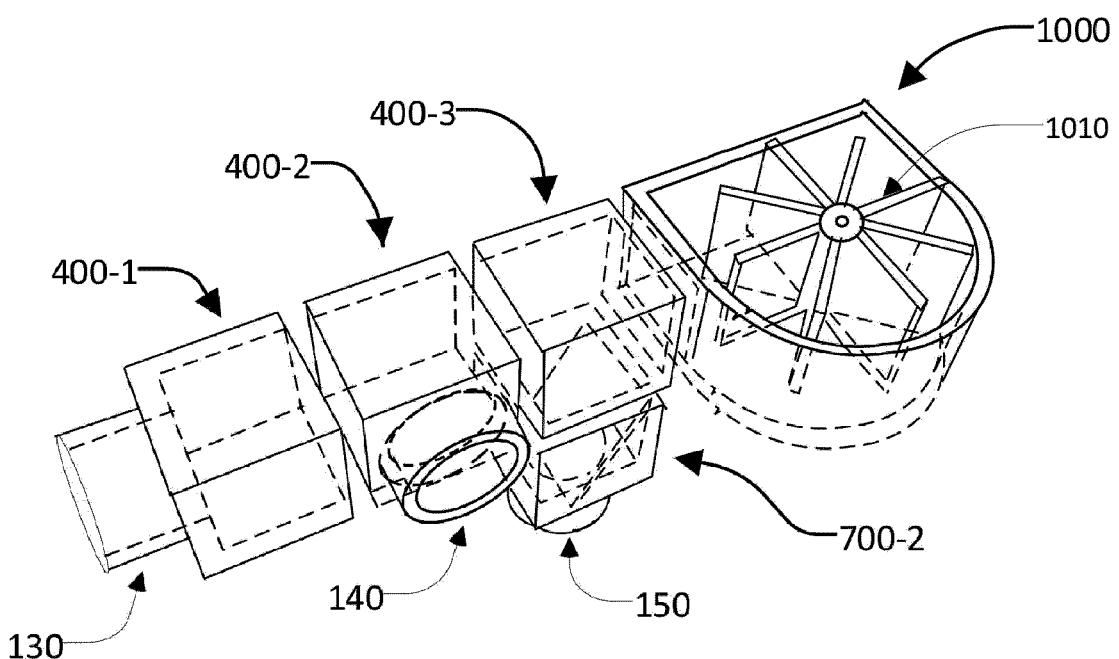
FIG. 10A shows an example of a volumetric breath quantifying module configured to separate a breath sample into sub-samples.
Figure 10B:
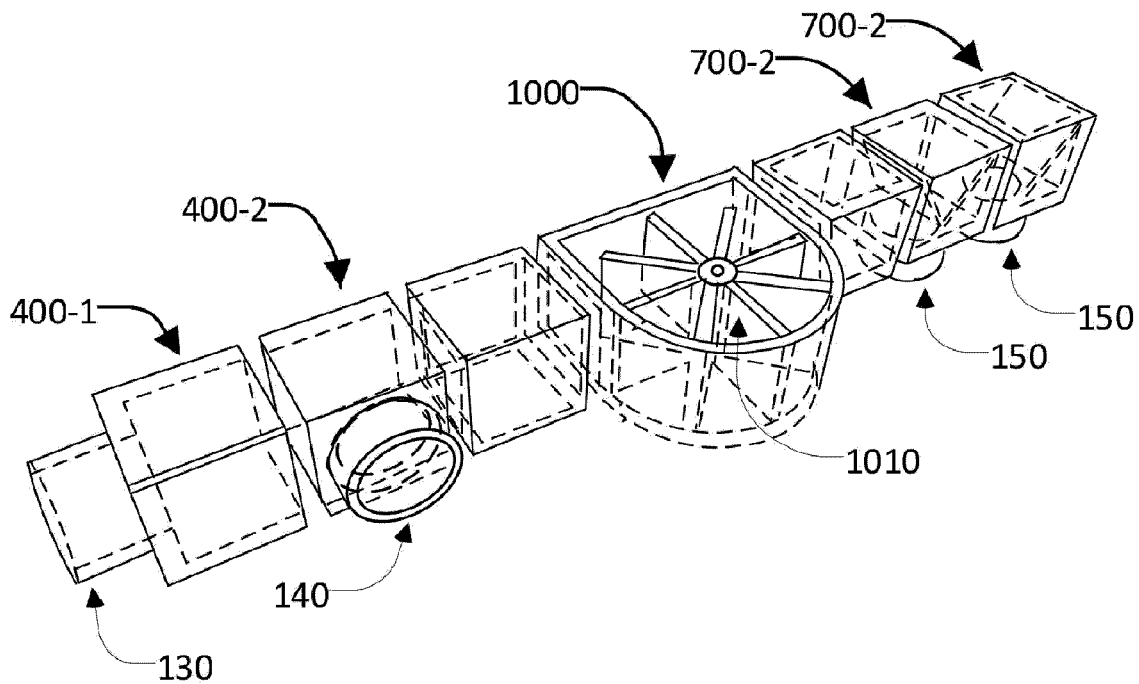
FIG. 10B shows an example of a volumetric breath quantifying module configured to separate a breath sample into sub-samples.

Turning now to FIGS. 10A and 10B, the breath sampler 100 can comprise additional units, for example, disposed between the non-rebreather part 110 and the sample delivery part 120, or after the sample delivery part 120.

As shown in FIG. 10A, in some embodiments, the breath sampler 100 can further comprise a volumetric breath quantifier 1000. The volumetric breath quantifier 1000 can be configured to measure a volume of breath exhaled by the patient and delivered through the sample collection chamber 200. For example, a volumetric breath quantifier can be disposed downstream of the sample collection chamber 200 (and the return inlet 195) and can be configured to measure a volume of breath passing through the downstream portion of the sample delivery part 120 to the exhaust 180. The volumetric breath quantifier can comprise one or more rotatably mounted blades or sails 1010 (e.g. in the form of a turnstile) configured to be driven about a spindle by airflow through the blades. The total rotation of the sails about the spindle can be determined and the airflow through the exhaust (and thus through the liquid capture medium) can be calculated or estimated. Estimation of the airflow through the liquid capture medium can be used to determine the sampling time required to collect a viable sample of breath from a patient.

As shown in FIG. 10B, the breath sampler 100 can alternatively comprise a volumetric breath quantifier 1000 positioned between the one-way outlet valve 160 and the sample outlet 190.

In some embodiments, the volumetric breath quantifier 1000 can be configured to divide the breath sample into a plurality of sub-samples, such that a sub-sample can be selectively delivered to the sample collection chamber 200. For example, the volumetric breath quantifier 1000 can be configured to deliver only a second sub-sample to the sample collection chamber 200, by controlling the flow of air through the sample outlet 190 based on the estimated (or calculated) volume of breath that has passed through the volumetric breath quantifier.

In an exemplary embodiment, the volumetric breath quantifier 1000 can comprise a turnstile 1010 configured to rotate as the patient exhales. The turnstile 1010 can be configured to drive a Geneva gear, which in turn controls air flow though the sample outlet 190. The Geneva gear can be configured to open a valve closing the sample outlet 190 when a predetermined volume of breath has passed through the volumetric breath quantifier 100. By selectively delivering only a sub-sample of exhaled air to the sample collection chamber 200, breath from the lower respiratory tract can be selectively delivered to the sample collection chamber 200.

Figure 10C:
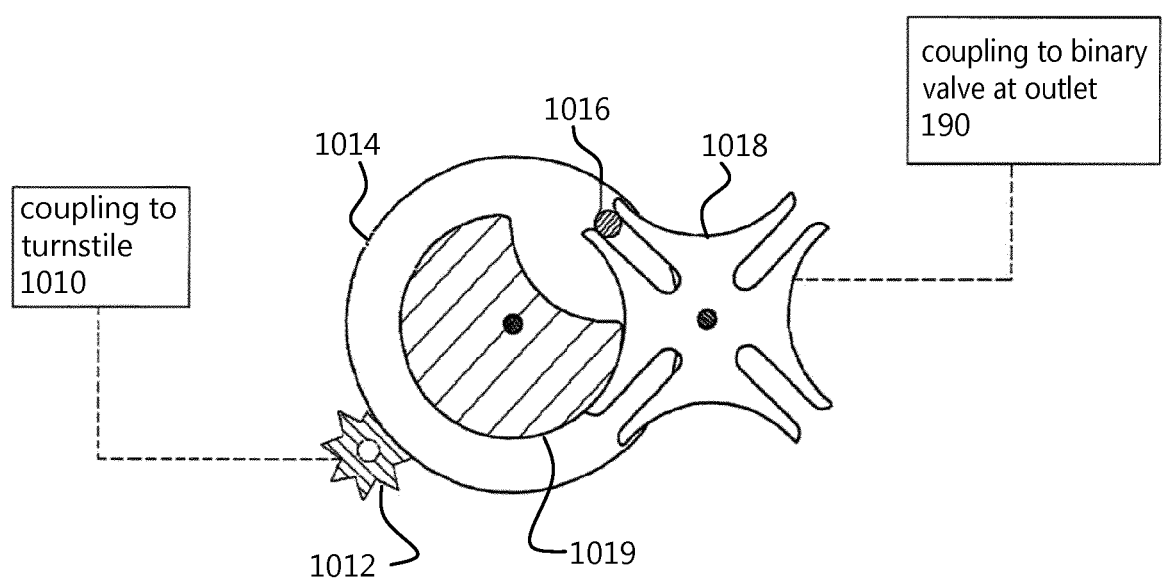
FIG. 10C show an exemplary gear mechanism suitable for use with the volumetric breath quantifying module shown in FIGS. 10A and 10B.

An exemplary gear mechanism for selectively opening the outlet 190 is shown in FIG. 10C. As shown in FIG. 10C, the turnstile 1010 can be coupled to a first gear 1012 such that rotation of the turnstile 1010 drives rotation of first gear 1012. First gear 1012 is configured to drive a second gear 1014, which forms part of a Geneva drive assembly. The second gear 1014 comprises a pin 1016, which is configured to engage a slot in the Geneva gear 1018. Rotation of the second gear 1014 moves the pin 1016 along the slot in the Geneva gear 1018, thereby rotating the Geneva gear 1018. A locking element 1019 prevents rotation of the Geneva gear 1018 until the pin 1016 approaches the end of the slot.

As shown in FIG. 10C, the Geneva gear 1018 is coupled to a binary valve, which closes the outlet 190 until the pin rotates the Geneva gear 1018. Since the movement of the turnstile 1010 is driven by the volume of breath passing through the device, the gear mechanism shown above can be configured to open the outlet 190 only when a predetermined volume of breath has passed through the turnstile 1010.

The gears can be configured such that a predetermined number of rotations of the turnstile 1010 triggers opening of the sample outlet 190. Thus, the device can be configured such that only breath from e.g. the lower respiratory tract is delivered to the liquid capture medium.

It will also be understood that the gear mechanism shown in FIG. 10C can also be configured to close the sample outlet 190 after delivery of a predetermined volume of breath therethrough. In such embodiments, the sample outlet 190 is open in an initial position, and the Geneva is configured to close the sample outlet 190 after delivery of a predetermined volume of breath.

The arrangement shown in FIGS. 10A-10C is a non-limiting example of a breath quantifier. As illustrated in FIG. 10A, turnstile 1010 comprises a plurality of panels arranged radially around a central point, about which rotation is facilitated. The number of panels and the volume defined between two panels of the turnstile 1010 can be configured according to preferred dimensional constraints for the device. The gear assembly and its coupling to the turnstile 1010 can be configured according to a physician's preference. For example, the gear mechanism and the turnstile 1010 can be configured such that the first 100 to 500 mL of breath, corresponding to the upper respiratory tract, can be isolated and directed to the open sample outlet 190, into the sample collection chamber 200 for sampling, and the remainder of the breath can be discarded. Alternatively, the breath from the upper respiratory tract can be discarded and the breath sample corresponding to air from the lower respiratory tract can be sampled for testing. In some embodiments, separate sample outlets 190 and sample collection chambers 200 can be provided for collecting first and second sub-samples (e.g. samples corresponding to breath from the upper and lower respiratory tracts respectively). In such embodiments, the Geneva gear can be configured to actuate two binary valves to open and close first and second sample outlets.

As a sampled exhaled breath enters volumetric breath quantifying module 1000, a first portion enters the breath quantifier 1000, causing the rotation of the turnstile 1010. The rotation of the turnstile 1010 can be measured (for example, by counting the number of full rotations or a number of partial rotations).

Whether the volumetric breath quantifier is intended for information purposes or whether it controls the flow of air to selectively deliver only a sub-sample of breath to the sample collection chamber 200 (as described with reference to FIG. 10B), the skilled person will appreciate that other volumetric quantifying methods are available and that opening and closing of the sample outlet 190 can be carried out mechanically (via Geneva gear or other mechanical linkage) or using electronically controlled components. For the purposes of the present invention, mechanical control of the breath sampler is preferred because of the disposable nature of the parts.

As is illustrated in the example of FIG. 10B, breath sampler 100 may be provided with a plurality of second modules 700, for example by means of a plurality of sub-modules 700-2. The provision of a plurality of second modules 700 enables multiple samples to be collected effectively simultaneously. The multiple samples may each correspond to a different portion of breath corresponding to a particular region of the respiratory tract. As shown in FIG. 10A, the sample inlet 130, one-way air inlet 140 are comprised in separate modules. This allows a care giver to configure the device for a particular patient, for example to include a module with a delivery port 510 for patients that may benefit from broncho-dilating nebulisers, etc.

In addition to showing the volumetric breath flow sampler 1000, FIGS. 10A and 10B also show an exemplary modular construction of the sampler 100 that can be applied to all embodiments. As shown in FIGS. 10A and 10B, each of the non-rebreather part 110 and the sample delivery part 120 can comprise multiple interconnectable components.

Figure 11:
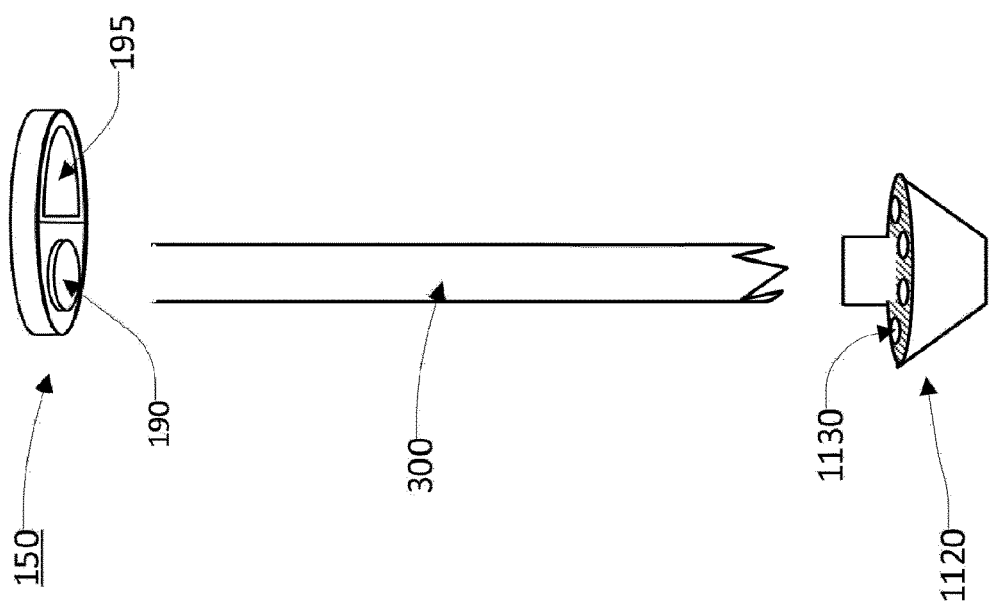
FIG. 11 shows an example of a tube for use in a sample collection chamber.

To further enhance the yield of substances of interest in the liquid capture medium, the breath samplers according to the present invention may further comprise a diffuser 1120 at the open distal end of the sample delivery tube 300, as shown in FIG. 11. The diffuser 1120 is configured to split the breath flow from the sample delivery tube 300 into multiple breath flow streams below the surface of the liquid capture medium 310. By splitting the flow of air into multiple streams, the surface area of the sample in contact with the liquid capture medium 310 is increased.

Advantageously, the solid volume occupied by the diffuser can also be used to maximise the flow of air through the liquid capture medium (relative to the volume of the liquid capture medium), by reducing the volume of liquid capture medium 310 within the tube. By maximising the dimensions of the diffuser relative to the interior of the sample collection chamber 200, and splitting the breath flow into multiple pathways, the volume of liquid in the sample collection chamber 200 can be reduced without drastically reducing the surface area of the airflow in contact with the liquid capture medium 310.

Figure 13:
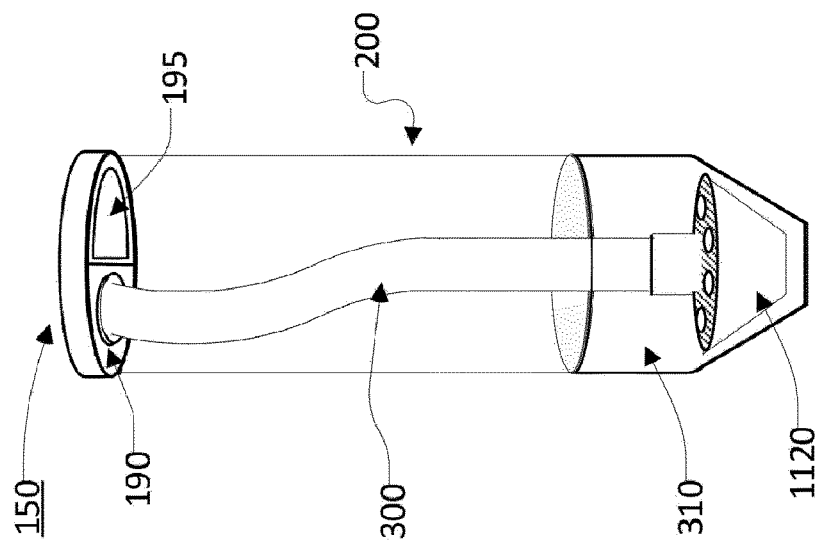
FIG. 13 show the sample collection chamber comprising a diffuser in the liquid capture medium.
Figure 12:
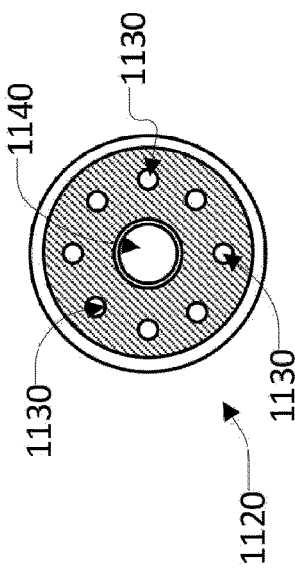
FIG. 12 shows an example of a diffuser head of a tube for use in a sample collection chamber.

As shown in FIG. 12, the diffuser 1120 can comprise a connection 1140 for the sample delivery tube 300 and a plurality of apertures 1130 in fluid communication with the connection 1140. FIG. 13 shows the diffuser 1120 in situ below the surface of the liquid capture medium 310 in the sample collection chamber 200.

Figure 14:
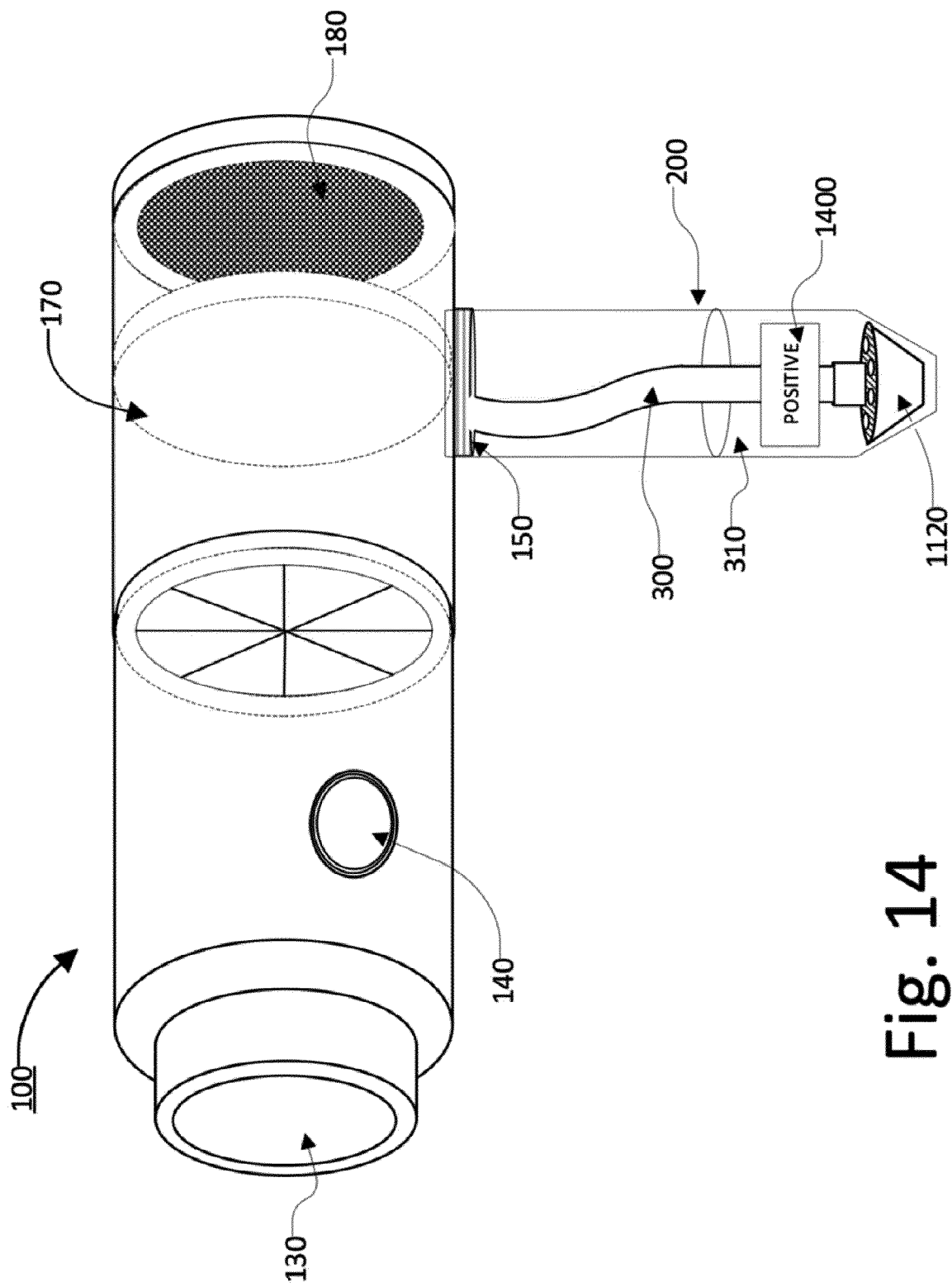
FIG. 14 shows an embodiment of the invention comprising an integrated analyser for detecting target biomarkers.

Referring now to FIG. 14, in some embodiments, the present invention can comprise an integrated analyser 1400. The analyser can comprise a lab-on-chip type analysis system including PCR amplification and electronic detection of target entities, lateral flow immunographic assays and other techniques that will be apparent to the person skilled in the art. PCR amplification and detection systems are known in the art. In the context of the present invention, the lab-on-chip diagnostic system can receive a sample of liquid capture medium after via an entry port (not-shown) after the patient has delivered a breath sample through the liquid capture medium. Alternatively, a volume of liquid capture medium can be delivered by a healthcare professional or in an automated manner to a point-of-care diagnostic device.

For example, the presence of a host and/or a pathogen in a captured breath sample can be instantly determined through the use of lateral flow assays and isothermal PCR. In another example, inflammatory markers may be measured in the captured breath sample. An unambiguous result may then be displayed in an LCD coupled to the integrated analysis module or can be relayed to a connected electronic device with a display. The analyser may preferably be configured to detect a naturally induced host or pathogen.

The skilled person will understand that the examples and embodiments described above may be combined in any feasible combination. The examples and embodiments described herein serve to illustrate rather than limit the invention. The person skilled in the art will appreciate that further alternative embodiments can be achieved without departing from the scope of the present disclosure, as defined by the appended claims.

The invention claimed is:

1. A breath sampler for collecting a breath sample from a patient, the breath sampler comprising:
a non-rebreather part comprising:
a sample inlet;
a one-way outlet valve arranged to allow air to exit the non-rebreather part, the one-way outlet valve and the sample inlet defining a first portion of an internal breath flow pathway therebetween; and
an air inlet comprising a plurality of slits in a wall of the breath sampler and arranged to be closed by a one-way inlet valve arranged to allow air to enter the non-rebreather part, the air inlet being in fluid communication with the first portion of the internal breath flow pathway; and
a sample delivery part in fluid communication with the non-rebreather part at an upstream end via the one-way outlet valve, the sample delivery part defining a second portion of the internal breath flow pathway, the sample delivery part comprising:
an air diverter, in the sample delivery part, arranged to divide the sample delivery part into an upstream portion and a downstream portion;
a sample outlet in the upstream portion;
a return inlet in the downstream portion and in fluid communication with an exhaust; and
a sample collection chamber connector configured to form a seal with an opening of a sample collection chamber, the connector defining a perimeter, the sample outlet and the return inlet being disposed within the perimeter;
wherein the breath sampler further comprises the sample collection chamber coupled to the sample collection chamber connector, the sample collection chamber comprising a liquid capture interface,
wherein the breath sampler is configured so that, during operation, the breath sample from the patient passes through the non-rebreather part, is delivered via the sample delivery part to the sample outlet into the sample collection chamber, passes through the liquid capture interface in the sample collection chamber, which captures at least one of chemical markers and biological markers from the breath sample, the breath then re-enters the sample delivery part from the sample collection chamber via the return inlet, and escapes the breath sampler via the exhaust.

2. The breath sampler according to claim 1, further comprising a sample delivery tube coupled to the sample outlet for delivering the breath sample to the liquid capture interface, and wherein the sample delivery tube is removably connected to the sample outlet.

3. The breath sampler according to claim 2, further comprising a diffuser coupled to the sample delivery tube, the diffuser comprising an inlet and a network of channels to divide the breath sample from the inlet into a plurality of streams.

4. The breath sampler according to claim 1, wherein the air diverter comprises a wall extending in a plane that is transverse to the longitudinal axis of the sample delivery part.

5. The breath sampler according to claim 1, further comprising a volumetric breath quantifier configured to measure a volume of breath delivered to the sample outlet.

6. The breath sampler according to claim 5, wherein the volumetric breath quantifier is configured to separate the breath sample into at least two sub-samples.

7. The breath sampler according to claim 6, wherein the volumetric breath quantifier further comprises a closure member configured to selectively close the sample outlet to prevent a first sub-sample being delivered to the sample collection chamber.

8. The breath sampler according to claim 7, wherein the volumetric breath quantifier comprises a Geneva gear configured to open the closure member when a predetermined volume of breath has entered the volumetric breath quantifier.

9. The breath sampler according to claim 8, wherein the volumetric breath quantifier is positioned downstream of the outlet valve and comprises:
- a turnstile rotatably mounted within the breath flow pathway and comprising at least one fin configured to be rotatably displaced by a defined breath volume;
- a geared coupling between the turnstile and the Geneva gear;
- wherein the turnstile is configured to move the Geneva gear from a first position to a second position, and
- wherein movement of the Geneva gear from the first position to the second position is configured to open the closure member to allow a second sub-sample to be delivered to the sample collection chamber.

10. The breath sampler according to claim 1, further comprising a plurality of selectively connectable modules.

11. The breath sampler according to claim 10, wherein:
- a first module comprises the non-rebreather part, the one-way outlet valve and the one-way air inlet; and
- a second module comprises the sample delivery part and the sample collection chamber connector.

12. The breath sampler according to claim 1, further comprising a delivery port in fluid communication with the non-rebreather part, configured for connection to a nebuliser.

13. The breath sampler according to claim 1, wherein the sample collection chamber further comprises an integrated testing module.

14. The breath sampler according to claim 13, wherein the integrated testing module is a lab-on-chip device.

15. The breath sampler according to claim 13, wherein the integrated testing module comprises a PCR unit.

16. The breath sampler according to claim 1, wherein at least one of the non-rebreather part and the sample delivery part comprises a sensor configured to measure additional biomarkers including one or more of: nucleic acids, cytokines, chemokines, C-reactive protein, hosts and pathogens.

17. The breath sampler according to claim 1, wherein the exhaust comprises a filter or mesh.

18. The breath sampler according to claim 1, further comprising a breath sampler cap configured to removably attach to a distal end of the breath sampler, the distal end of the breath sampler being an end opposite to an end comprising the sample inlet.

19. The breath sampler according to claim 18, wherein the sampler cap is arranged to cover the exhaust.

20. The breath sampler according to claim 18, wherein the sampler cap comprises connection means corresponding to the sample collection chamber.

* * * * *